US011229396B2

(12) United States Patent
Himmrich

(10) Patent No.: US 11,229,396 B2
(45) Date of Patent: Jan. 25, 2022

(54) METHOD AND MEDICAL DEVICE FOR DISCRIMINATING BETWEEN A SUPRAVENTRICULAR TACHYCARDIA AND A VENTRICULAR TACHYCARDIA

(71) Applicants: Medtronic, Inc., Minneapolis, MN (US); Ewald Himmrich, Selzen (DE)

(72) Inventor: Ewald Himmrich, Selzen (DE)

(73) Assignee: Medtronic, Inc., Minneapolis, MN (US)

( * ) Notice: Subject to any disclaimer, the term of this patent is extended or adjusted under 35 U.S.C. 154(b) by 176 days.

(21) Appl. No.: 15/567,735

(22) PCT Filed: Apr. 20, 2015

(86) PCT No.: PCT/IB2015/000523
§ 371 (c)(1),
(2) Date: Oct. 19, 2017

(87) PCT Pub. No.: WO2016/170379
PCT Pub. Date: Oct. 27, 2016

(65) Prior Publication Data
US 2018/0132745 A1    May 17, 2018

(51) Int. Cl.
*A61B 5/363*        (2021.01)
*A61N 1/362*        (2006.01)
(Continued)

(52) U.S. Cl.
CPC ............... *A61B 5/363* (2021.01); *A61B 5/25* (2021.01); *A61B 5/316* (2021.01); *A61B 5/35* (2021.01);
(Continued)

(58) Field of Classification Search
CPC . A61B 5/0464; A61B 5/0456; A61B 5/04012; A61B 5/0408; A61B 5/7264;
(Continued)

(56) References Cited

U.S. PATENT DOCUMENTS 3,554,187 A * 1/1971 Glassner ............ A61B 5/04012
600/516
8,924,736 B1 * 12/2014 Dusan ..................... G06F 21/32
340/5.52
(Continued)

FOREIGN PATENT DOCUMENTS

WO        9965570 A1    12/1999
WO       03047690 A2     6/2003
(Continued)

OTHER PUBLICATIONS

International Search Report and Written Opinion from International Application No. PCT/IB2015/000523, dated Jan. 14, 2016, 13 pp.
Rhoades et al., "Medical Physiology: Principles for Clinical Medicine," Third Edition, 2009 (Applicant points out, in accordance with MPEP 609.04(a), that the year of publication, 2009, is sufficiently earlier than the effective U.S. filing date, so that the particular month of publication is not in issue.) pp. 237-240.
(Continued)

*Primary Examiner* — Michael W Kahelin
*Assistant Examiner* — Elizabeth K So
(74) *Attorney, Agent, or Firm* — Shumaker & Sieffert, P.A.

(57) ABSTRACT

A method for automatically discriminating between a supraventricular tachycardia event and a ventricular tachycardia event is provided. The method includes sensing a first cardiac signal using a first electrode pair and a second cardiac signal using a second electrode pair during a heartbeat, applying a first algorithm to the first cardiac signal to determine whether the first cardiac signal is indicative for a supraventricular tachycardia or indicative for the ventricular tachycardia; applying a second algorithm to the second cardiac signal to determine whether the second cardiac signal is indicative for the supraventricular tachycardia or indicative for the ventricular tachycardia, the second comparison algorithm being different from the first comparison algorithm; and assigning to a heartbeat-specific indicator a first value indicative for the ventricular tachycardia when at least one of the first cardiac signal and the second cardiac
(Continued)

signal have been determined to be indicative tor the ventricular tachycardia.

46 Claims, 20 Drawing Sheets

(51) Int. Cl.
*A61B 5/00* (2006.01)
*A61B 5/25* (2021.01)
*A61B 5/35* (2021.01)
*A61B 5/316* (2021.01)
*A61B 5/352* (2021.01)

(52) U.S. Cl.
CPC .............. *A61B 5/352* (2021.01); *A61B 5/686* (2013.01); *A61B 5/6869* (2013.01); *A61B 5/7264* (2013.01); *A61N 1/3622* (2013.01); *A61N 1/3624* (2013.01); *A61N 1/3627* (2013.01)

(58) Field of Classification Search
CPC ... A61B 5/04525; A61B 5/6869; A61B 5/686; A61B 5/00; A61B 5/0452; A61N 1/3624; A61N 1/3622; A61N 1/3627; A61N 1/04; A61N 1/362
See application file for complete search history.

(56) References Cited

U.S. PATENT DOCUMENTS

| | | | |
|---|---|---|---|
| 2004/0049238 A1* | 3/2004 | Jarverud | A61B 5/053 607/17 |
| 2004/0093035 A1 | 5/2004 | Schwartz et al. | |
| 2005/0149125 A1 | 7/2005 | Kim et al. | |
| 2009/0259124 A1* | 10/2009 | Rothenberg | A61B 5/0422 600/424 |
| 2010/0249627 A1 | 9/2010 | Zhang et al. | |

FOREIGN PATENT DOCUMENTS

| | | |
|---|---|---|
| WO | 2011136923 A1 | 11/2011 |
| WO | 2016170379 A1 | 10/2016 |

OTHER PUBLICATIONS

International Preliminary Report on Patentability from International Application No. PCT/IB2015/000523, dated Oct. 24, 2017, 8 pp.
Examination Report from counterpart European Application No. 15721831.4, dated May 6, 2021, 4 pp.
Response to Examination Report dated May 6, 2021, from counterpart European Application No. 15721831.4, filed Aug. 31, 2021, 25 pp.

* cited by examiner

13011

| FF-indicator | + | + | − | − |
|---|---|---|---|---|
| NF-indicator | + | − | + | − |
| Result | vt | vt | vt | svt |

1001

| | | |
|---|---|---|
| 1050: | indicator array = [0,0,0,0,0,0,0,0] |
| 1201: | 1st indicator = 1 |
| 1202: | 2nd indicator = 1 |
| 1300: | indicator array[max] = 1st vt-indicator \|\| 2nd vt-indicator |
| | -> indicator array = [0,0,0,0,0,0,0,1] |
| 1500: | shl(indicator array) |
| | -> indicator array = [0,0,0,0,0,0,1,0] |

| | | |
|---|---|---|
| 1201: | 1st indicator sequenz | = (1, 1, 1, 0, 0, 1, 0, 1) |
| 1202: | 2nd indicator sequenz | = (1, 0, 0, 1, 0, 0, 1, 0) |
| 1300: | indicator array | = [1, 1, 1, 1, 0, 1, 1, 1] |
| 1400: | Σ indicator array[i] > 5 ? | |
| | -> activate stimulation | |

FIG 9B

METHOD AND MEDICAL DEVICE FOR DISCRIMINATING BETWEEN A SUPRAVENTRICULAR TACHYCARDIA AND A VENTRICULAR TACHYCARDIA

This application is a national stage entry under 35 U.S.C. § 371 of PCT Application No. PCT/IB2015000523, which was filed on Apr. 20, 2015, and is incorporated herein by reference in its entirety.

TECHNICAL FIELD

Embodiments of the present invention relate to methods for automatically discriminating between supraventricular tachycardia and ventricular tachycardia, and to medical devices implementing the methods, in particular to implantable medical devices (IMDs) such as cardiac pacemakers and implantable cardioverter-defibrillators (ICDs).

BACKGROUND

Proper cardiac function relies on the synchronized contractions of the heart. When normal cardiac rhythm is initiated at the sinoatrial node, the heart is said to be in sinus rhythm. However, when the heart experiences irregularities in its coordinated contraction, due to electrophysiological disturbances caused by a disease process or from an electrical disturbance, the heart is said to be arrhythmic. The resulting cardiac arrhythmia impairs cardiac efficiency and may even be a life threatening event.

Cardiac pacemakers and implantable cardioverter-defibrillators monitor the heart of the patient via electrodes carried by one or more implantable leads and may provide therapeutic electrical stimulation to the heart if required. The leads are typically implanted transvenously, i.e., implanted in the heart through one or more veins, sometimes referred to as endocardial leads.

Monitoring the heart may include sensing signals representative of intrinsic depolarizations of the heart and analyze the sensed signals to identify normal or abnormal rhythms. Upon detection of an abnormal rhythm, the device may deliver an appropriate electrical stimulation signal or signals to restore or maintain a more normal rhythm. For example, an IMD may be expected to deliver cardioversion or defibrillation shocks to the heart upon detecting a treatable tachycardia or fibrillation.

Treatable arrhythmias refer to abnormal rhythms for which delivery of stimulation therapy to one or both of the ventricles is indicated. Treatable arrhythmias may include ventricular tachycardia (VT) or ventricular fibrillation (VF) occurring in the ventricular region of the heart. Ventricular tachycardia can quickly degenerate into ventricular fibrillation (VF). Ventricular fibrillation is a condition characterized by extremely rapid, non-synchronous contractions of the ventricles. This condition is fatal unless the heart is returned to sinus rhythm within a few minutes.

Non-treatable arrhythmias, on the other hand, refer to abnormal rhythms that typically do not require stimulation therapy to be delivered to either of the ventricles. Non-treatable arrhythmias may include supra-ventricular tachycardia (SVT). In some instances, non-treatable arrhythmias may go untreated, i.e., no stimulation therapy is delivered to the heart. In other instances, non-treatable arrhythmias may be treated using stimulation therapy, but the stimulation therapy is not delivered to the ventricles of the patient.

Accurately determining whether a tachycardia is ventricular (VT) or supra-ventricular (SVT) prevents inadvertent delivery of therapy to a ventricle of the patient when no therapy to the ventricle is necessary (e.g., in the case of a rhythm mischaracterized as a treatable arrhythmia) or withholding stimulation therapy when the therapy to the ventricle is necessary (e.g., in the case of a rhythm mischaracterized as a non-treatable arrhythmia). Unnecessary delivery of stimulation therapy to the patient may be uncomfortable for the patient, needlessly depletes the power source of the medical device and, in some patients or circumstances, can even induce more dangerous arrhythmias.

For these and other reasons, there is a need for the present invention.

SUMMARY

According to an embodiment, a method for automatically discriminating between a supraventricular tachycardia event and a ventricular tachycardia event is disclosed. The method includes: sensing a first cardiac signal during a heartbeat using a first electrode pair and a second cardiac signal during the heartbeat using a second electrode pair, the second electrode pair having a different distance between its electrodes than the first electrode pair; applying a first comparison algorithm to the first cardiac signal to determine whether the first cardiac signal is indicative for a supraventricular tachycardia or indicative for the ventricular tachycardia; applying a second comparison algorithm to the second cardiac signal to determine whether the second cardiac signal is indicative for the supraventricular tachycardia or indicative for the ventricular tachycardia, wherein the second comparison algorithm differs from the first comparison algorithm; and assigning to a heartbeat-specific indicator a first value that is indicative for the ventricular tachycardia when at least one of the first cardiac signal and the second cardiac signal is determined to be indicative for the ventricular tachycardia.

According to an embodiment, a method of operating a medical device is disclosed. The method includes: recording a far-field cardiac signal and a near-field cardiac signal of the same heartbeat; searching for a deviation of the near-field cardiac signal from a patient-specific near-field template with respect to S-waves that is indicative for a ventricular tachycardia, and searching for a deviation of the far-field cardiac signal from a patient-specific far-field template at least with respect to R-waves that is indicative for the ventricular tachycardia; and classifying the heartbeat as being indicative for a supraventricular tachycardia when no deviation that is indicative for the ventricular tachycardia has been found during searching, otherwise the heartbeat is identified as being indicative for a ventricular tachycardia.

According to an embodiment, a method of controlling a power consumption of an implantable medical device having an electrode pair is disclosed. The method includes: recording a first signal for determining QRS-wave morphology parameters and a second signal for determining S-wave morphology parameters for each heartbeat of a sequence of heartbeats; comparing for each of the heartbeats the first signal with a first template to determine if changes of the QRS-wave morphology parameters are indicative for a supraventricular tachycardia; comparing for each of the heartbeats the second signal with a second template to determine if changes of the S-wave morphology parameters are indicative for the supraventricular tachycardia; and refraining from applying an electric stimulation signal to the electrode pair when each of the changes of S-wave morphology parameters and each of the changes of QRS-wave morphology parameters are indicative for the supraventricular tachycardia for at least a predefined number of the heartbeats of the sequence of heartbeats.

According to an embodiment, a method of treating tachycardia is disclosed. The method includes: determining a far-field EGM signal relating to a heartbeat; determining a near-field EGM signal relating to the same heartbeat; comparing the far-field EGM signal with a far-field template EGM signal to determine first changes related to positive waves and negative waves; comparing the near-field EGM signal with a near-field template EGM signal to determine second changes related to negative waves; assigning to a heartbeat-specific indicator a first value that is indicative for a ventricular tachycardia when at least one of the first changes and the second changes is indicative for the ventricular tachycardia; and using the heartbeat-specific indicator to determine if an electric stimulation signal is to be delivered to at least two stimulation electrodes.

According to an embodiment, a method for automatically discriminating between a supraventricular tachycardia event and a ventricular tachycardia event is disclosed. The method includes: recording two EGM-signals representing different spatial summation of action potential signals during a heartbeat; using an algorithm to determine if morphology parameters of waves in each of the two EGM-signals are indicative for a ventricular tachycardia; and classifying the heartbeat as being indicative for the ventricular tachycardia when at least one of the morphology parameters is determined to be indicative for the ventricular tachycardia and as being indicative for supraventricular tachycardia when none of the morphology parameters is determined to be indicative for the ventricular tachycardia.

According to an embodiment, a method for automatically discriminating between a supraventricular tachycardia event and a ventricular tachycardia event is disclosed. The method includes: sensing a first cardiac signal during a heartbeat using a first electrode pair and a second cardiac signal during the heartbeat using a second electrode pair, the second electrode pair having a different distance between its electrodes than the first electrode pair; applying a first comparison algorithm to the first cardiac signal using a first template to determine whether the first cardiac signal is indicative for a supraventricular tachycardia or indicative for the ventricular tachycardia; applying a second comparison algorithm to the second cardiac signal using a second template to determine whether the second cardiac signal is indicative for the supraventricular tachycardia or indicative for the ventricular tachycardia, wherein the second comparison algorithm differs from the first comparison algorithm; and assigning to a heartbeat-specific indicator a first value that is indicative for the ventricular tachycardia when at least one of the first cardiac signal and the second cardiac signal is determined to be indicative for the ventricular tachycardia.

The methods explained herein are typically performed by an implantable medical device (IMD), in particular an implantable pacemaker and/or an implantable cardioverter-defibrillator, more typical by a controller of such an IMD.

Typically, a processor of the controller executes suitable software code stored on a computer readable storage medium to perform the methods explained herein.

According to an embodiment, a medical device is disclosed. The medical device includes: a first electrode pair, a second electrode pair having a different distance between its electrodes than the first electrode pair, and a controller connected with the first electrode pair and the second electrode pair. The controller is configured to use the first electrode pair to determine a first cardiac signal of a heartbeat, to use the second electrode pair to determine a second cardiac signal of the heartbeat, to apply a first comparison algorithm to the first cardiac signal and a first template to determine whether the first cardiac signal is indicative for a supraventricular tachycardia or indicative for a ventricular tachycardia; to apply a second comparison algorithm to the second cardiac signal and a second template to determine whether the second cardiac signal is indicative for the supraventricular tachycardia or indicative for the ventricular tachycardia, wherein the second comparison algorithm is different from the first comparison algorithm, and classifying the heartbeat as being indicative for the ventricular tachycardia when at least one of the first cardiac signal and the second cardiac signal is determined to be indicative for the ventricular tachycardia.

Those skilled in the art will recognize additional features and advantages upon reading the following detailed description, and upon viewing the accompanying drawings.

BRIEF DESCRIPTION OF THE DRAWINGS

The components in the figures are not necessarily to scale, instead emphasis being placed upon illustrating the principles of the invention. Moreover, in the figures, like reference numerals designate corresponding parts. In the drawings:

FIG. 9A illustrates method steps of a method of automatically discriminating between an SVT-event and a VT-event according to an embodiment;

FIG. 9B illustrates further method steps of the method illustrated in FIG. 8A according to an embodiment;

DETAILED DESCRIPTION

Figure 1:
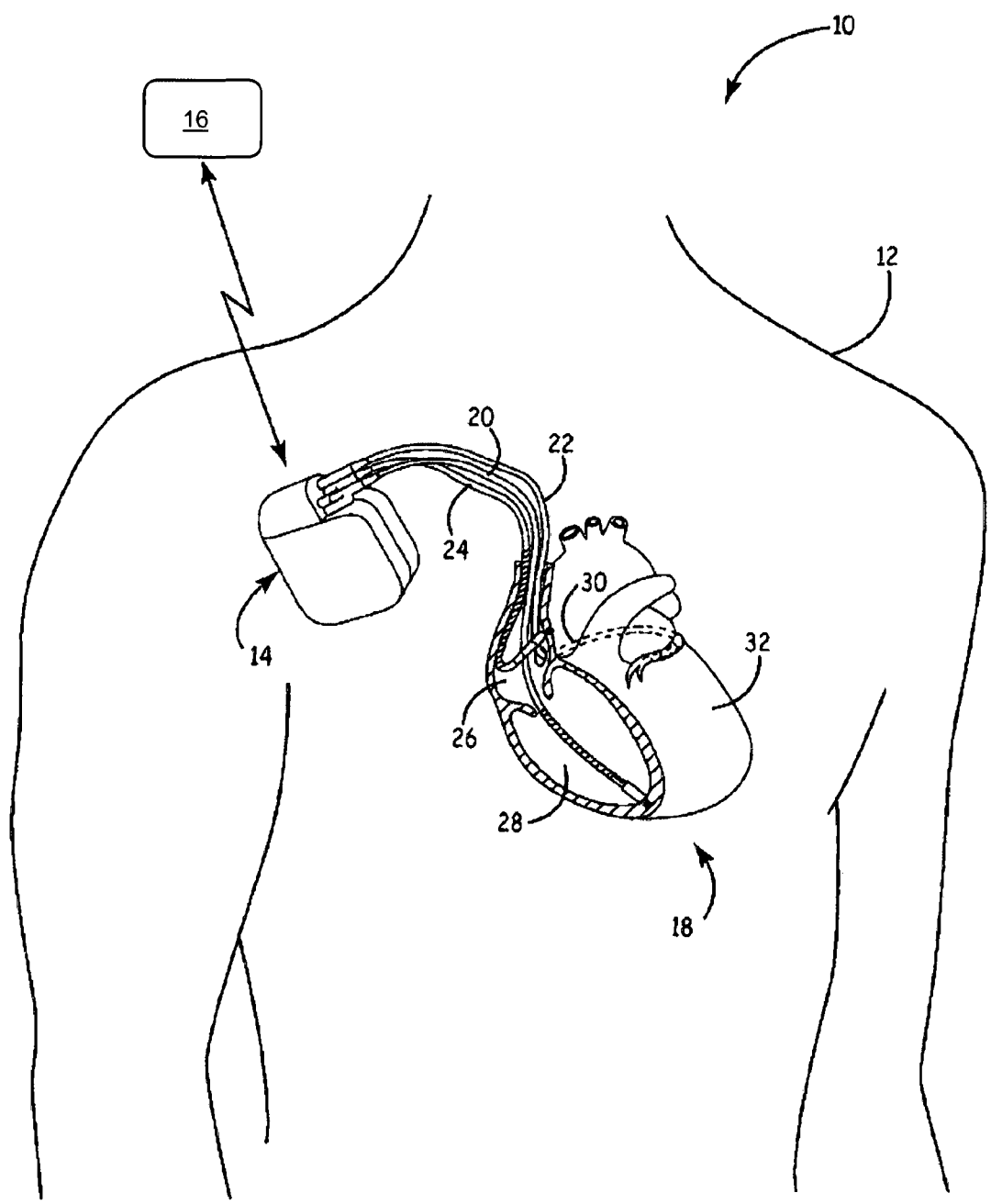
FIG. 1 is a conceptual diagram illustrating a therapy system including an IMD that may be used to provide therapy to patient according to an embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Reference will now be made in detail to various embodiments, one or more examples of which are illustrated in the Figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appending claims. The drawings are not scaled and are for illustrative purposes only. For clarity, the same elements or method steps have been designated by the same references in the different drawings if not stated otherwise.

Automated (rule-based) tachycardia discriminating algorithms, in particular rule-based automated tachycardia discriminating algorithms for discriminating between treatable and non-treatable arrhythmias and implantable medical devices (IMDs) employing these algorithms are disclosed.

The term "treatable arrhythmia", as used herein, refers to any tachycardia that is ventricular in origin and can potentially be treated by delivering a therapy in at least one of the ventricles for terminating the ventricular tachycardia such as anti-tachycardia pacing or ventricular cardioversion or defibrillation shocks. Typically, delivery of stimulation therapy to one or both of the ventricles is indicated for a treatable arrhythmia, in particular for a ventricular tachycardia. A "non-treatable" arrhythmia as described herein is any tachycardia for which delivery of stimulation therapy to one or both of the patient's ventricles is not indicated. The non-treatable arrhythmia may be tachycardia with a relatively slow ventricular rate (below a ventricular tachycardia detection rate) and/or a non-sustained ventricular tachycardia and/or a tachycardia that is supraventricular in origin.

The term "ventricular tachycardia" (VT) as used in this specification intends to describe a heart condition characterized by a rapid heartbeat of e.g. 150 to 270 or more beats per minute that has its origin in some abnormal location within the ventricular myocardium. The abnormal location typically results from damage to the ventricular myocardium from a myocardial infarction. Ventricular tachycardia is a potentially life-threatening arrhythmia as it may lead to ventricular fibrillation, asystole, and sudden death.

The term "supra-ventricular tachycardia" (SVT) as used in this specification intends to describe a heart condition characterized by a rapid heartbeat of e.g. 150 to 270 or more beats per minute that has its origin at or above the atrioventricular node. The "SVT" may be due to any supraventricular cause. An SVT may be a sinus tachycardia, atrial tachycardia (AT), an atrial fibrillation (AF), an atrial flutter, an atrioventricular nodal reentrant tachycardia (AVNRT), or an atrioventricular reciprocating tachycardia (AVRT).

Automated tachycardia discriminating algorithms described herein employ comparing two substantially simultaneously sensed or recorded EGM signals ("electrograms"), typically a relatively global EGM signal and a relatively more local EGM signal, with respective templates of normal patient's heartbeats for applying rules on a beat-by-beat basis to gain and/or accumulate evidence of ventricular tachycardia (VT). The templates may be template signals, e.g. EGM signals of normal heartbeats, or parameters derived therefrom.

The terms "substantially simultaneously sensed signals" and "substantially simultaneously recorded signals" as used in this specification intends to describe that a time shift between the signals is less than four milliseconds (ms), more typically less than two milliseconds, and even more typically less than one millisecond when stored in a digitized form. Typically, the signals are sensed or recorded in parallel.

The relatively global EGM signal is also referred to herein as the far-field (FF) signal in that at least one of the typically two sensing electrodes is placed away from the ventricular chambers to obtain a signal representing the spatial summation of action potential signals as they occur over a larger area of the ventricles. Likewise, the relatively more local EGM signal is also referred to herein as the near-field (NF) signal in that the sensing electrodes are (both) located in or on a ventricular chamber to obtain a more local ventricular EGM signal.

Due to comparing two substantially simultaneously sensed EGM signals representing different spatial summation of action potential signals of the same heartbeat with corresponding template signals of normal heartbeats, the reliability in discriminating between VT and SVT may be increased.

Within this specification the two electrodes used for sensing the far-field signal are also referred to as first electrode pair and first electrodes, respectively, and the two electrodes used for sensing the near-field signal are also referred to as second electrode pair and second electrodes, respectively. As the second electrodes are, compared with the first electrodes, used for sensing a cardiac signal representing a smaller spatial summation of action potential signals, the second electrodes have typically a smaller electrode distance than the first electrode electrodes, more typically a smaller distance between the tips of its electrodes.

FIG. 1 is a conceptual diagram illustrating an exemplary therapy system 10 that may be used to provide therapy to a patient 12. Therapy system 10 includes an implantable medical device (IMD) 14 and leads 20, 22 and 24 that extend from IMD 14. Therapy system 10 may also include a programming device 16 that wirelessly communicates with IMD 14 as indicated by the double arrow.

In the exemplary embodiment illustrated in FIG. 1, IMD 14 is an implantable cardiac device that may provide electrical stimulation therapy to a heart 18 of patient 12. The electrical stimulation therapy to heart 18, sometimes referred to as cardiac rhythm management therapy, may include pacing, cardioversion, defibrillation and/or cardiac resynchronization therapy (CRT). As such, IMD 14 may operate as an implantable pacemaker, cardioverter, and/or defibrillator, e.g. as an implantable cardioverter-defibrillator (ICD). The electrical stimulation therapy provided by IMD 14 typically depends on the arrhythmia detected by IMD 14, as described in further detail below.

Methods and devices described herein, however, should not be interpreted as being limited to any particular implantable medical device or any particular cardiac medical device. Instead, embodiments may include any cardiac medical device so long as the device utilizes a plurality of electrodes or other sensors for monitoring the cardiac rhythm of a patient. The cardiac medical device shall be configured to determine cardiac EGMs (intracardiac ElectroGraMs) using the electrodes. The electrodes are typically capable of directly sensing the cardiac EGMs.

IMD 14 delivers the electrical stimulation therapy to heart 18 via one or more electrodes located on leads 20, 22 and/or 24 and implanted within or adjacent to one or more atria or ventricles of heart 18. In the exemplary embodiment illustrated in FIG. 1, leads 20, 22 and 24 are coupled to IMD 14 and extend into heart 18 of patient 12. More particular, right ventricular (RV) lead 20 extends through one or more veins (not shown), the superior vena cava (not shown), and right atrium 26, and into right ventricle 28 of heart 18. Left ventricular (LV) coronary sinus lead 22 extends through one or more veins, the vena cava, right atrium 26, and into the coronary sinus 30 to a region adjacent to the free wall of left ventricle 32 of heart 18. Right atrial (RA) lead 24 extends through one or more veins and the vena cava, and into the right atrium 26 of heart 18. In other embodiments, IMD 14 may deliver stimulation therapy to heart 14 by delivering stimulation to an extravascular tissue site in addition to or instead of delivering stimulation via electrodes of intravascular leads 20, 22 and 24.

In addition to delivering therapy to heart 18, electrodes of leads 20, 22 and 24 may sense electrical signals attendant to depolarization and repolarization of heart 18 (e.g., cardiac signals). IMD 14 may analyze the sensed signals to monitor a rhythm of the heart to detect and classify an arrhythmia of heart 18. As described above, the electrical stimulation therapy provided by IMD 14 may depend on the type of tachycardia detected by IMD 14. For example, IMD 14 provides stimulation therapy (e.g., ATP, defibrillation shock and/or cardioversion shock) to ventricle 28 of patient 12 in response to detecting that the rhythm is a treatable arrhythmia, in particular VT or VF. Further, IMD 14 typically withholds delivery of stimulation therapy to ventricle 28 in response to detecting that the rhythm is a non-treatable arrhythmia, in particular SVT. Instead, IMD 14 typically delivers no therapy when an SVT-event is detected. Alternatively, stimulation therapy may be provided to atrium 26 to treat the detected SVT.

In some instances, SVT may be conducted to ventricles 28 and/or 32. This is one reason which makes discriminating between VT and SVT demanding. An SVT conducted to ventricles and falsely detected as VT, would result in IMD 14 delivering ventricular stimulation therapy (e.g., ATP, cardioversion or defibrillation) when no ventricular therapy is needed. Unnecessary delivery of electrical stimulation therapy to ventricles 28 and/or 32 may be uncomfortable for patient 12 and, in some patients, may induce dangerous arrhythmias. Additionally, delivery of unnecessary electrical stimulation therapy needlessly depletes the power source of IMD 14. It is desirable, therefore, to avoid delivering a therapy to ventricles 28 and/or 32 due to inappropriate arrhythmia detection.

The techniques of this disclosure typically increase the accuracy with which IMD 14 discriminates between VT and SVT at same or even better sensitivity of detecting VT.

In the following, the accuracy of a technique or algorithm in discriminating between VT and SVT is also referred to as specificity of the technique or algorithm, respectively.

Typically, the sensitivity and specificity may be given in percentages (%). Ideally, a technique or algorithm has both a sensitivity of 100% (i.e. each VT is correctly detected, not falsely classified as SVT) and a specificity of 100% (i.e. each SVT is correctly detected, not falsely classified as VT). Whether a technique or algorithm produces the correct classification is measured against a trained cardiologist. When both specificity and sensitivity are 100%, each VT may be treated and any unnecessary electrical stimulation avoided.

In accordance with techniques described in this disclosure, IMD 14 uses two different substantially simultaneously recorded electrical depolarization/repolarization signals from a heartbeat (each of the signals is also referred to as "cardiac signal" and "electrogram" or EGM, respectively), and classifies the heartbeat as being indicative for VT when at least one of the two cardiac signals is determined to be indicative for VT. To determine if the cardiac signals are indicative for VT, the cardiac signals are compared with respective patient-specific templates, which are representative for normal (sinus) electrical depolarization/repolarization signals of the patient heartbeat or morphology parameters thereof. Typically, several heartbeats of a tachycardia have to be indicative for VT to classify the tachycardia as VT. For this purpose, heartbeat-specific indicators for storing whether a heartbeat is indicative for VT or SVT may be used by IMD 14.

It is found that an algorithm which bases the discrimination between VT and SVT on two different cardiac signals of one or more heartbeats is superior compared to other algorithms with respect to specificity at the same or an even higher sensitivity.

A user, such as a physician, technician, or other clinician, may interact with programming device 16 to communicate with IMD 14. For example, the user may interact with programming device 16 to retrieve physiological or diagnostic information from IMD 14. For example, the user may use programming device 16 to retrieve information from IMD 14 regarding the rhythm of the heart of patient 12, trends therein over time, or cardiac arrhythmia episodes. As another example, the user may use programming device 16 to retrieve information from IMD 14 regarding other sensed physiological parameters of patient 12, such as electrical depolarization/repolarization signals from the heart (EGMs), intracardiac or intravascular pressure, activity, posture, respiration or thoracic impedance. As another example, the user may use programming device 16 to retrieve information from IMD 14 regarding the performance or integrity of IMD 14 or other components of therapy system 10, such as leads or a power source of IMD 14.

The user may also interact with programming device 16 to program IMD 14, e.g., select values for operational parameters of IMD 14. For discriminating types of tachycardia, for example, the user may interact with programming device 16 to program one or more sets of parameters used by comparison algorithm(s) or search algorithm(s), select electrodes or sensors for use in detecting cardiac signals of patient 12 heart 18. By programming these parameters, the physician or other user can attempt to improve accuracy of discriminating tachycardia types. For this purpose, the physician or other user may inspect retrieved cardiac arrhythmia episodes and classifications of the episodes made by IMD 14. Upon detecting a misclassification, the physician or other user, in particular a cardiologist may adjust parameters of the algorithm(s) such as detecting windows for the waves in the cardiac signal(s). This is explained in detail below.

For electrical stimulation therapies, for example, the user may interact with programming device 16 to program one or more sets of therapy parameters, select therapy programs or progressions of therapy programs to be used during particular arrhythmias, select an electrode or combination of electrodes of leads 20, 22 and 24 to use for delivering electrical stimulation (pulses or shocks), select parameters for the electrical pulse or shock (e.g., pulse amplitude, pulse width, or pulse rate), or the like. By programming these parameters, the physician or other user can attempt to generate an efficacious therapy for patient 12 that is delivered via the selected electrodes.

Programming device 16 may be a dedicated hardware device with dedicated software for programming of IMD 14. Alternatively, programming device 16 may be an off-the-shelf computing device running an application that enables programming device 16 to program IMD 14. In some examples, programming device 16 may be a handheld computing device or a computer workstation. Programming device 16 may, in some instances, include a programming head that may be placed proximate to the patient's body near the implant site of IMD 14 in order to improve the quality or security of communication between IMD 14 and programming device 16. Programming device 16 may include a user interface that receives input from the user and/or displays data to the user.

Programming device 16 may communicate with IMD 14 via wireless communication using any techniques known in the art. Examples of communication techniques may include, for example, magnetic telemetry, low frequency telemetry or radiofrequency (RF) telemetry, but other techniques are also contemplated. In some instances, programming device 16 and IMD 14 may communicate in the 402-405 MHz frequency band in accordance with the Medical Implant Communications Service (MICS) protocol.

Figure 2:
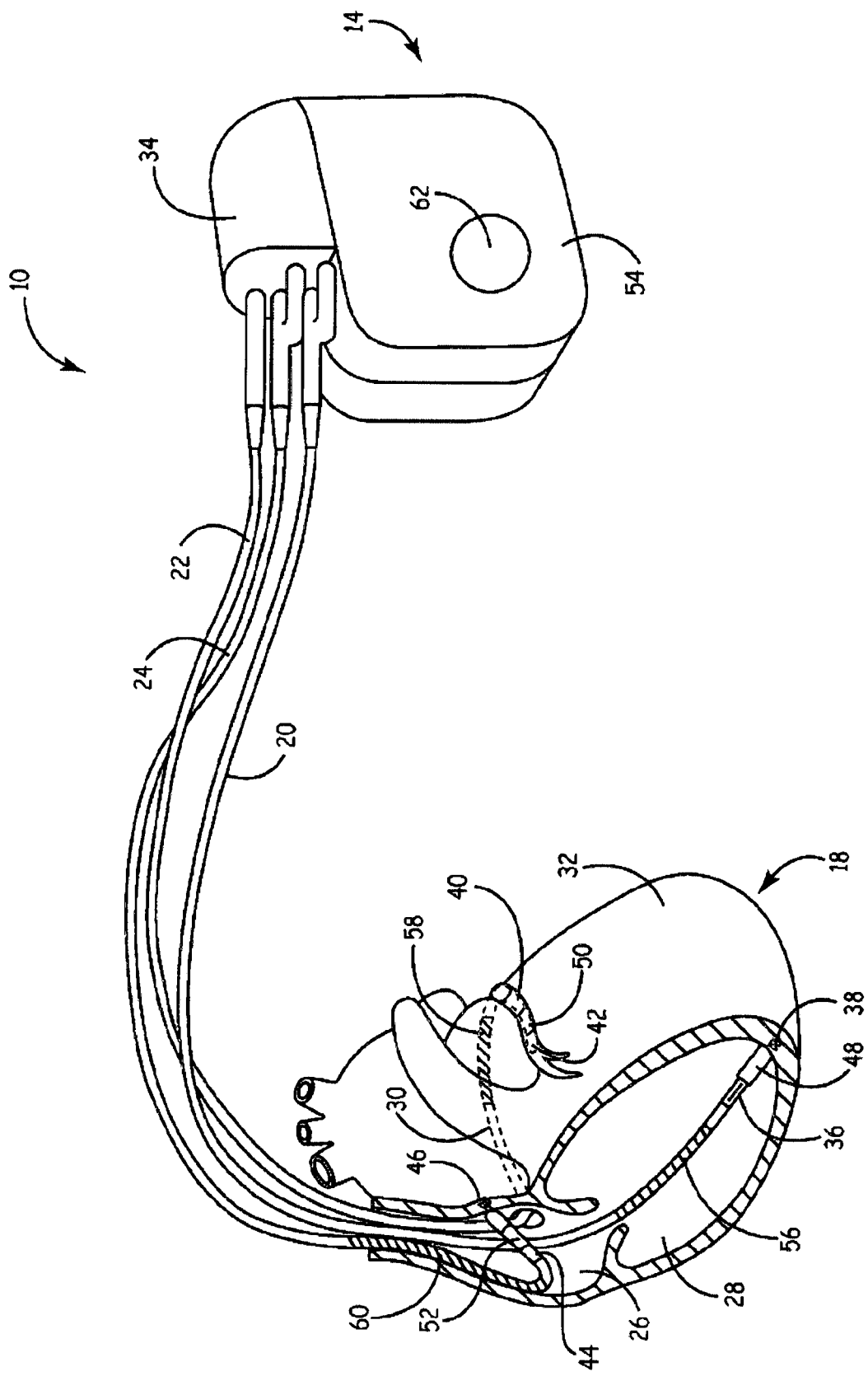
FIG. 2 is a conceptual diagram illustrating the IMD and leads of the therapy system of FIG. 1 in greater detail.

FIG. 2 is a conceptual diagram illustrating IMD 14 and leads 20, 22 and 24 of therapy system 10 in greater detail. Leads 20, 22 and 24 are electrically coupled to a stimulation module, a sensing module, or other modules of IMD 14 via connector block 34. In some examples, proximal ends of leads 20, 22 and 24 include electrical contacts that electrically couple to respective electrical contacts within connector block 34. In addition, in some examples, leads 20, 22 and 24 are mechanically coupled to connector block 34 with the aid of set screws, connection pins or another suitable mechanical coupling mechanism.

Each of the leads 20, 22 and 24 typically includes an elongated (electrically) insulating lead body, which may carry a number of concentric coiled conductors separated from one another by tubular insulating sheaths. Other lead configurations are also contemplated, such as lead configurations that do not include coiled conductors, but instead a different type of conductor. In the illustrated example, bipolar electrodes 36 and 38 are located proximate to a distal end of lead 20. In addition, bipolar electrodes 40 and 42 are located proximate to a distal end of lead 22 and bipolar electrodes 44 and 46 are located proximate to a distal end of lead 24.

Electrodes 36, 40, and 44 may take the form of ring electrodes, and electrodes 38, 42, and 46 may take the form of extendable helix tip electrodes mounted retractably within insulating electrode heads 48, 50, and 52, respectively. Each of the electrodes 36, 38, 40, 42, 44, and 46 is electrically coupled to a respective one of the conductors within the lead body of its associated lead 20, 22 and 24, and thereby coupled to respective ones of the electrical contacts on the proximal end of leads 20, 22 and 24. In other embodiments, electrodes 36, 38, 40, 42, 44, and 46 may be other types of electrodes.

Electrodes 36, 38, 40, 42, 44, and 46 may sense electrical signals attendant to the depolarization and repolarization of heart 18. The electrical signals are conducted to IMD 14 via the one or more conductors of respective leads 20, 22 and 24. In some examples, IMD 14 also delivers pacing pulses via electrodes 36, 38, 40, 42, 44, and 46 to cause depolarization of cardiac tissue of heart 14. In some examples, as illustrated in FIG. 2, IMD 14 includes one or more housing electrodes, such as housing electrode 62, which may be formed integrally with an outer surface of hermetically-sealed housing 54 of IMD 14 or otherwise coupled to housing 54. In some examples, housing electrode 62 is defined by an uninsulated portion of an outward facing portion of housing 54 of IMD 14. In some examples, housing electrode 62 comprises substantially all of housing 54. Divisions between insulated and uninsulated portions of housing 54 may be employed to define two or more housing electrodes. Any of the electrodes 36, 38, 40, 42, 44, and 46 may be used for unipolar sensing or pacing in combination with housing electrode 62. As such, the configurations of electrodes used by IMD 14 for sensing and pacing may be unipolar or bipolar depending on the application.

Leads 20, 22 and 24 typically also include elongated electrodes 56, 58, and 60, respectively, which may, in some instances, take the form of a coil. IMD 14 may deliver high energy electrical shocks, e.g., defibrillation or cardioversion shocks, to heart 18 via any combination of elongated electrodes 56, 58, and 60, and housing electrode 62. In particular, IMD 14 may deliver the high energy electrical shocks in response to determining that a detected arrhythmia is treatable. Electrodes 36, 38, 40, 42, 44, 46, 56, 58, 60, and 62 may be fabricated from any suitable electrically conductive material, including, but not limited to, platinum, platinum alloy or other materials known to be usable in implantable defibrillation electrodes.

The configuration of therapy system 10 illustrated in FIGS. 1 and 2 are merely examples. In other examples, therapy system 10 may include more or fewer leads extending from IMD 14. For example, IMD 14 may be coupled to two leads, e.g., one lead implanted within right atrium 26 and the other implanted within right ventricle 28. In another example, IMD 14 may be coupled to a single lead that is implanted within either an atrium or ventricle of heart 18. As a further example, the therapy system may include three transvenous leads located as illustrated in FIGS. 1 and 2, and an additional lead located within or proximate to left atrium 32. As such, IMD 14 may be used for single chamber or multi-chamber cardiac rhythm management therapy. In addition to more or fewer leads, each of leads 20, 22 and 24 may include more or fewer electrodes.

In still other examples, a therapy system may include epicardial leads and/or patch electrodes instead of or in addition to the transvenous leads 20, 22 and 24 illustrated in FIGS. 1 and 2. In other words, IMD 14 may be a subcutaneous cardiac device. Further, IMD 14 need not be implanted within patient 12. In examples in which IMD 14 is not implanted in patient 12, IMD 14 may deliver defibrillation pulses and other therapies to heart 18 via percutaneous leads that extend through the skin of patient 12 to a variety of positions within or outside of heart 18.

Figure 3:
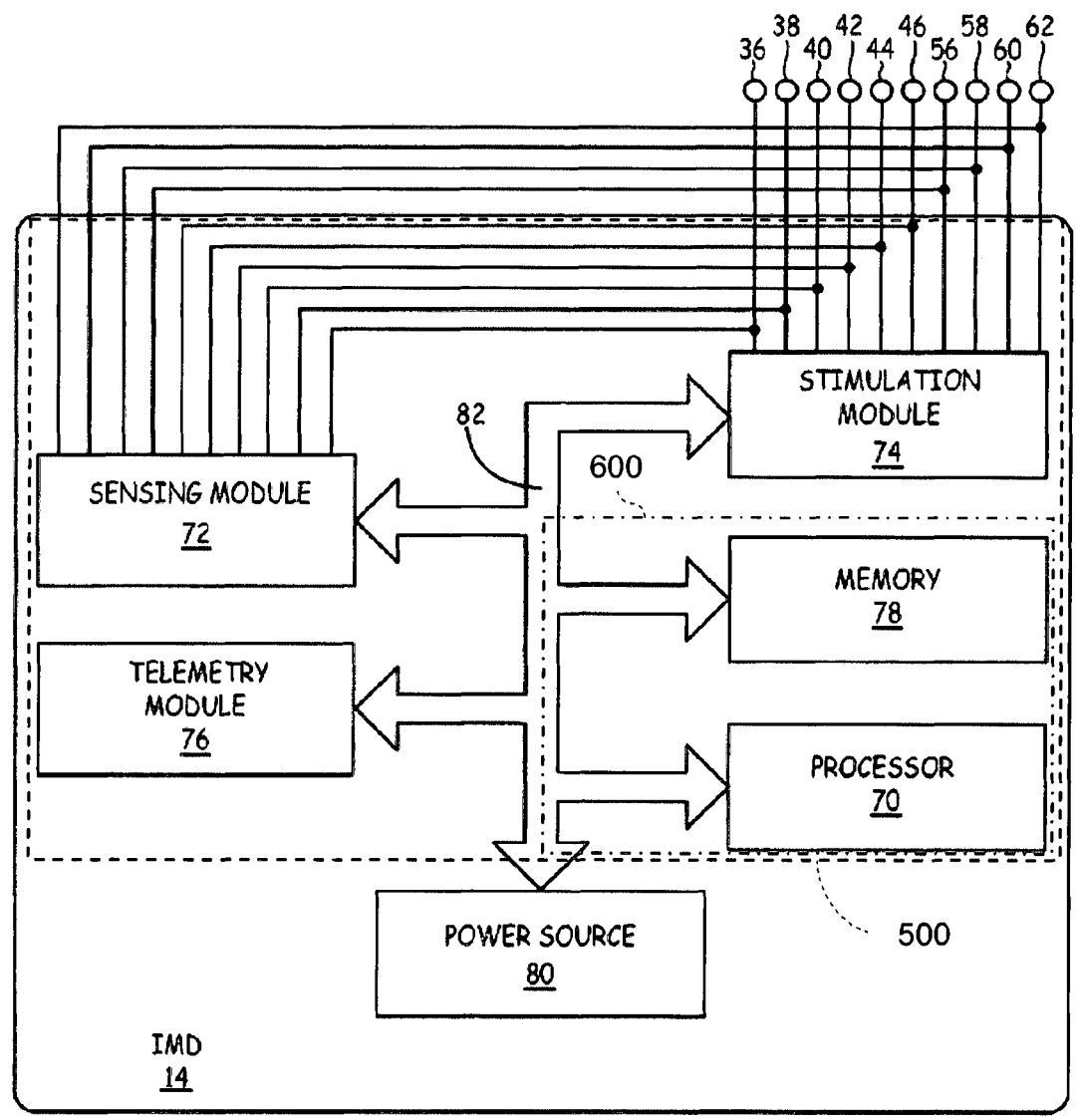
FIG. 3 is a functional block diagram of a configuration of components of an IMD according to an embodiment.

FIG. 3 is a functional block diagram of an exemplary configuration of components of IMD 14. Typically, IMD 14 includes a processor 70, a sensing module 72, a stimulation module 74, a telemetry module 76, a memory 78, and a power source 80. Processor 70, sensing module 72, stimulation module 74, telemetry module 76, and a memory 78 may be considered to form a controller 500 of IMD 14. The various components of IMD 14 and controller 500, respectively, are interconnected by a data bus 82. In other examples, the various components of IMD 14 may be interconnected by a number of point-to-point connections or a combination of one or more data buses and one or more point-to-point connections. For example, there may be a typically particularly fast data bus between processor 70 and memory 78 or portion thereof forming a computing module or analysis module 600 of IMD 14 and controller 500, respectively.

Processor 70 may include one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Memory 78 may include computer-readable instructions that, when executed by processor 70, cause components of IMD 14 to perform various functions attributed to the respective components in this disclosure. Memory 78 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 14 are coupled to power source 80, which may include a non-rechargeable battery, rechargeable storage device such as a rechargeable battery or capacitor (which may be recharged internally or transcutaneously with the use of electromagnetic or piezoelectric transformers), energy-harvesting device, or a combination thereof. A non-rechargeable battery may be capable of holding a charge for several years, while a rechargeable battery may be inductively charged from an external device, e.g., on a daily or weekly basis. Power source 80 also may include power supply circuitry (not shown in FIG. 3) for providing regulated voltage and/or current levels to power the components of IMD 14.

Processor 70 controls electrical stimulation module 74 to deliver stimulation therapy to heart 18. Processor 70 may control electrical stimulation module 74 to deliver stimulation according to a selected one or more therapy programs, which may be stored in memory 82. For example, processor 70 may control electrical stimulation module 74 to deliver electrical pacing pulses, cardiac resynchronization pulses, or cardioversion or defibrillation shocks with the amplitudes, pulse widths, frequencies, and/or electrode polarities specified by the selected therapy programs. The type of therapy program provided may, for example, be dependent on the type of arrhythmia detected, whether a previous therapy program was effective, or the like.

Electrical stimulation module 74 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. Electrical stimulation module 74 may include a switch module (not shown in FIG. 3) and processor 70 may use the switch module to select, e.g., via a data/address bus 82, which of the available electrodes to us to deliver pacing, resynchronization, cardioversion, or defibrillation pulses/shocks. The switch module may include a switch array, switch matrix, multiplexer, or any other type of switching device suitable to selectively couple stimulation energy to selected electrodes.

Sensing module 72 is configured to receive signals sensed by one or more sensors connected to sensing module 72. Sensing module 72 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. In this case, electrodes 36, 38, 40, 42, 44, 46, 56, 58, 60, and 62 are the sensors connected to sensing module 72. Sensing module 72 may include a switch module and processor 80 may use the switch module to select, e.g., via a data/address bus 82, which of the available electrodes are used to sense electrical cardiac signals of heart 18. In this manner, sensing module 72 is capable of monitoring signals from a variety of electrode sensing vectors formed by different combinations of electrodes 36, 38, 40, 42, 44, 46, 56, 58, 60, and 62. The switch module may include a switch array, switch matrix, multiplexer, or any other type of switching device suitable to selectively couple the selected electrodes to the sensing circuitry of sensing module 72. In some instances, sensing module 72 and therapy module 74 may share a switch module. Accordingly, one or more of electrodes 36, 38, 40, 42, 44, 46, 56, 58, 60, and 62 may be used for sensing and applying electrical stimulation.

Sensing module 72 may receive signals sensed by various other sensors instead of, or in addition to, the signals sensed by the combinations of electrodes 36, 38, 40, 42, 44, 46, 56, 58, 60 and 62. For example, sensing module 72 may receive signals from one or more sensors that sense intravascular pressure, blood pressure, blood flow, acceleration, displacement, motion, respiration, or blood/tissue chemistry such as oxygen saturation, carbon dioxide, pH, protein levels, enzyme levels or other physiological parameter. Sensing module 72 may couple to these various other sensors via a wired connection or a wireless connection, e.g., using telemetry module 76.

Sensing module 72 may store the sensed signals in memory 78. In some instances, sensing module 72 may store the sensed signals in raw form. In other instances, sensing module 72 may process the sensed signals and store the processed signals in memory 78. For example, sensing module 72 may amplify, filter and/or digitize the sensed signal and store the digitized signal in memory 78. The signals stored by sensing module 72 may be retrieved and further processed by processor 70. Additionally, processor 70 may control telemetry module 76 to send the signals stored by sensing module 72 or in memory 74 to another device, such as programming device 16 or a monitoring device.

Under the control of processor 70, telemetry module 76 may receive data from and send data to programming device 16 with the aid of an antenna, which may be internal and/or external to IMD 14. Telemetry module 76 may include any suitable hardware, firmware, software or any combination thereof for communicating with another device. For example, telemetry module 76 may include appropriate modulation, demodulation, frequency conversion, filtering, and amplifier components for transmission and reception of data.

As described above, the electric stimulation (type of therapy program) provided by stimulation module 74 may be dependent on the type of heart rhythm detected, e.g., whether it is treatable (e.g., VT/VF) or non-treatable (e.g., SVT). Processor 70 controls stimulation module 74 to deliver electrical stimulation therapy to at least one ventricle of patient 12 in response to detecting the rhythm is treatable. For example, processor 70 may control stimulation module 74 to deliver a cardioversion shock in response to detecting VT or control stimulation module 74 to deliver a defibrillation shock in response to detecting VF. As another example, processor 70 may control stimulation module 74 to deliver anti-tachycardia pacing (ATP) to at least one ventricle of patient 12 in response to detecting VT. In other examples, processor 70 may control stimulation module 74 to deliver a progression of therapies, e.g., shocks with increasing energy levels or various anti-tachycardia pacing regimens followed by shocks in response to detecting the rhythm as treatable.

Rhythms detected to be non-treatable (e.g., SVT), on the other hand, do not require stimulation therapy to be delivered to the ventricles of patient 12. In fact, non-treatable rhythms may not be treated at all. In instances in which non-treatable rhythms are treated, however, stimulation module 74 does not deliver therapy to the ventricles of patient 12. Instead, stimulation module 74 may deliver therapy to other locations, including one or both atria.

Sometimes, a non-treatable arrhythmia, in particular SVT is conducted to the ventricles. Previously used automated rhythm classification techniques often falsely detected such a SVT as VT or VF, resulting in the delivery of ventricular cardioversion, defibrillation or ATP therapy when no ventricular therapy is needed. Unnecessary delivery of ventricular therapy is generally uncomfortable for patient 12, needlessly depletes power source 80 and can sometimes induce more dangerous arrhythmias (e.g., actual VT or VF). It is desirable, therefore, to avoid delivering a ventricular stimulation therapy due to inappropriate detection of ventricular arrhythmias.

In accordance with automated rhythm classification techniques of this disclosure, a first cardiac signal for determining QRS-wave morphology parameters (QRS-wave morphology parameter changes) of a heartbeat is compared with a first template. Furthermore, a second cardiac signal for determining S-wave morphology parameters (S-wave morphology parameter changes) of the same heartbeat is compared with a second template. The heartbeat is only classified as being indicative for SVT when none of the QRS-wave morphology parameters and none of S-wave morphology parameters are determined as being indicative for VT. Likewise, the heartbeat is classified as being indicative for VT when at least one of the QRS-wave morphology parameters and S-wave morphology parameters is determined as being indicative for VT. These techniques increase the reliability of discrimination between treatable VT and non-treatable SVT and reduce the likelihood of delivery of unnecessary electrical stimulation to heart 18 and particularly to the ventricles of heart 18.

In particular, processor 70 is configured to analyze the signals sensed by sensing module 72 to obtain morphology parameters that characterize the rhythm of heart 18 of patient 12. Processor 70 may analyze the rhythm over a period of time to generate a plurality of morphology parameters. Processor 70 typically analyzes the rhythm over a period of time that encompasses a single ventricular event, e.g., a 200 ms time window around a sensed ventricular event. As such, processor 70 may be considered as analyzing the rhythm on a beat-by-beat basis. Typically, a tachycardia is only classified as VT when at least a first number of heartbeats of a heartbeat sequence are indicative for VT, e.g. at least six out of eight heartbeats.

Typically, for several heartbeats processor 70 compares a far-field EGM signal and a near-field EGM signal to respective templates. The templates represent a normal (sinus) heartbeat of a patient. By way of comparison, changes of respective beat morphology parameters are obtained. Of particular interest are changes of beat-related far-field morphology parameters, typically QRS-morphology parameters, i.e. morphology parameters referring to the QRS-complex, and of near-field morphology parameters, typically morphology parameters of negative waves in the near-field signal, in particular near-field S-morphology parameters.

The term "QRS-complex" as used in this specification intends to describe the combination of central graphical deflections seen on a typical far-field EGM or a typical ECG (ElectroCardioGrams) corresponding to the depolarization of the ventricles of a heartbeat.

Figure 4:
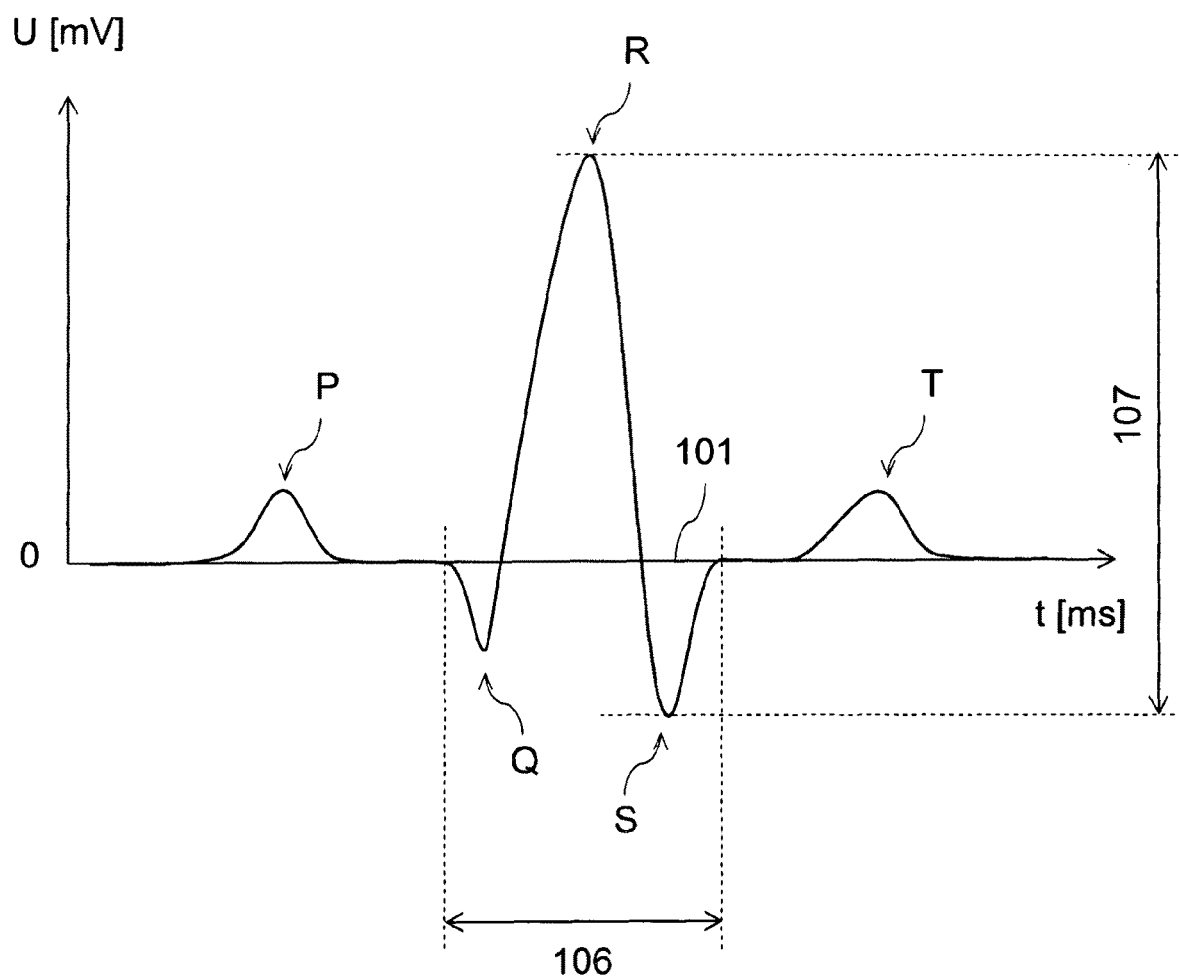
FIG. 4 is an schematic far-field EGM signal.

As illustrated in FIG. 4, a typical far-field EGM may have five deflections referred to as "P-wave" P, "Q-wave" Q, "R-wave" R, "S-wave" S and "T" wave T. The Q-wave Q is a downward deflection after the P-wave P reflecting an atrial depolarization. An R-wave R follows as an upward deflection, and the S-wave S is any downward deflection after an R-wave R. The T-wave T representing a ventricular repolarization follows the S-wave S. Sometimes, an additional U-wave (not shown in FIG. 4) representing repolarization of the Purkinje fibers of inner ventricular walls of the heart follows T-wave T.

Cardiologist use the appearance or morphology of the waves in EGMs and ECGs, respectively, in particular the shape of waves and the wave pattern, for distinguishing supraventricular tachycardia events and ventricular tachycardia events from each other. Reliably discriminating between supraventricular and ventricular tachycardia events requires a sufficiently experienced cardiologist and learning from many examples, respectively. Accordingly, cardiologists are usually not aware of the criteria used for discriminating between VT and SVT.

The methods described herein are based on studying a large number of patient's EGMs to extract morphology parameters of the waves including their duration and amplitude and combination of morphology parameters which are suited for an algorithmic approach resulting in a discrimination performance closer to trained cardiologist as compared to known algorithmic approaches such as wavelet based approaches and approaches utilizing time vector correlations in cardiac signals.

Typically, the Q-wave, the R-wave, and the S-wave form the QRS-complex 106. However, a QRS-complex corresponding to a heartbeat may not even include a Q-wave or may include a second upward deflection (second R-wave) to mention only two of the possible deviations from the "standard" QRS-pattern that may occur, in particular during a tachycardia.

In ECGs, QRS-complex 106 typically lasts from about 60 ms to about 100 ms, or even to about 120 ms for some patients. In far-field EGMs, QRS-complex 106 typically lasts from about 40 ms to about 100 ms. In near-field EGMs, QRS-complex 106 typically lasts from about 30 ms to about 80 ms. The amplitude 107 of QRS-complex (QRS-amplitude), i.e. sum of amplitude of R-wave R and S-wave S measured from base-line or iso-line 101, is typically in a range of a few mV (milli Volts), e.g. from about 5 mV to about 30 mV, in ECGs, far-field EGMs and near-field EGMs.

The term "QRS-morphology parameter" as used in this specification intends to describe any parameter describing the morphology of a QRS-complex relating to a heartbeat including the morphology of the waves present in the QRS-complex and their pattern or sequence.

QRS-morphology parameters (herein also referred to as first heartbeat-specific morphology parameters and far-field beat morphology parameters) may include number of Q-waves, width of Q-wave(s), amplitude of Q-wave(s), number of R-waves, width of R-wave(s), amplitude of R-wave(s), notching of R-wave(s), splitting of R-wave(s), number of S-waves, width of S-wave(s), amplitude of S-wave(s) as well as amplitude ratios, ratios between widths of different waves (also referred to as width ratios) and ratios between amplitude and width of the same or different waves (also referred to as amplitude-width ratios) in the far-field EGM. For example, QRS-morphology parameters may include an R-wave symmetry index (RSI) that represents the ratio of onset-side slope to offset-side slope of the R-wave in the far-field EGM, R-wave width (RW) value that represents the width of the R-wave in the far-field EGM, Q-wave R-wave index (QRI) that represents the ratio of the Q-wave amplitude to the R-wave amplitude in the far-field EGM, and an occurrence of a delta wave reflecting a premature upstroke of the QRS-complex due to an atrioventricular bypass tract.

The term "far-field morphology parameter" as used in this specification intends to describe any parameter describing the morphology of a signal or curve related to a heartbeat in a far-field representation, typically in a far-field EGM, including the QRS-morphology parameters.

Likewise, the term "near-field morphology parameter" (also referred to as second heartbeat-specific morphology parameter) as used in this specification intends to describe any parameter describing the morphology of a signal or curve related to a heartbeat in a near-field representation, typically a near-field EGM, including morphology parameters of negative waves, in particular S-waves in the near-field EGM (near-field S-morphology parameters).

Near-field S-morphology parameters may include number of S-waves, width of S-wave(s), and amplitude of S-wave(s) in the far-field EGM as well as ratios therebetween.

Near-field morphology parameters may include any of the near-field S-morphology parameters and any of the following near-field R-morphology parameters: number of R-waves, width of R-wave(s), and amplitude of R-wave(s) in the near-field EGM as well as ratios therebetween. Further, near-field morphology parameters may include rations between near-field S-morphology parameters and near-field R-morphology parameters.

For automatically discriminating between supraventricular tachycardia and ventricular tachycardia, a near-field cardiac signals and a far-field cardiac signal are compared with respective templates of the patient to search for changes or variations of the beat morphology parameters and to classify the changes or variations as being indicative of supraventricular tachycardia and ventricular tachycardia, respectively. This is described in more detail below.

Other types of morphology parameters may also be used in addition to the beat morphology parameters described above. For example, processor 70 may analyze the rhythm over a period of time (e.g., 3-second window) to compute any of a number of gross morphology parameters. The gross morphology parameters characterize the morphology of the EGM over the period of time and may include more than one beat. Beat morphology parameters, on the other hand, are morphology parameters of a single beat.

Moreover, other non-morphology parameters may also additionally be used such as heart rate, intracardiac or intravascular pressure, oxygen saturation, blood pressure, blood flow, tissue perfusion, impedance, heart sounds, motion or the like. In other words, IMD 14 may integrate information from hemodynamic sensors with EGM information or use the information from the hemodynamic sensors instead of the EGM information in determining whether a rhythm is treatable or non-treatable.

Each of the parameter changes (changes of near-field morphology parameters and changes of far-field morphology parameters) obtained by processor 70 has a different discrimination capability or probability to predict the condition. In other words, each of the parameters on its own may be indicative of whether the condition exists, e.g., whether a rhythm is of supraventricular or ventricular tachycardiac character.

However, none of the parameter changes on their own has been found to provide a perfect indication of whether a heartbeat is indicative for a supraventricular tachycardia.

Different thereto, some of the parameter changes on their own have been found to provide a strong indication for a ventricular tachycardia. However, this depends on the patient.

Furthermore, VTs are typically reflected in changes of QRS-morphology parameters while SVTs are typically not reflected in changes of QRS-morphology parameters. However, it is found that some VTs are not reflected in changes of QRS-morphology parameters and some SVTs are reflected in changes of QRS-morphology parameters.

Therefore, algorithmic techniques of this disclosure typically search for a combination of two or more than two parameter changes in the far-field (also referred to as first changes) and a different combination of two or more than two parameter changes in the near-field (also referred to as second changes) in making the classification as to whether the heartbeat is indicative for SVT (supraventricular tachycardia) or VT (ventricular tachycardia).

Furthermore, the determination as to whether the condition (VT or SVT) exists is typically determined by analyzing a sequence of e.g. eight consecutive heartbeats, sixteen consecutive heartbeats, or twenty-four consecutive heartbeats. However, the given sequence lengths are to be understood as non-limiting examples.

For example, a tachycardia may be determined as VT when at least 6 of eight consecutive heartbeats or at least eighteen of twenty-four consecutive heartbeats are classified as being indicative for VT. Otherwise the tachycardia may be determined as SVT.

Processor 70 controls stimulation module 74 to deliver a high energy shock (e.g., cardioversion or defibrillation shock) to heart 18 based upon the classification of the rhythm. If the rhythm is determined to be non-treatable (SVT), stimulation module 74 does not deliver electrical stimulation to the ventricles. Instead, stimulation module 74 may deliver therapy to one or both atria or provide no therapy at all. If the rhythm is determined to be treatable (VT), however, stimulation module 74 delivers ventricular stimulation therapy, e.g., in the form of ATP, cardioversion shock(s), defibrillation shock(s) or a combination thereof. Processor 70 may further analyze the rhythm to further differentiate the type of treatable arrhythmia. For example, processor 70 may, after classifying a tachycardia as non-SVT (VT), analyze the rate and regularity of the rhythm to determine whether the treatable rhythm is VT or already VF. In the case of VT, stimulation module 74 may provide ATP and/or cardioversion may be delivered. In the case of VF, stimulation module 74 may deliver a defibrillation shock.

Figure 5:
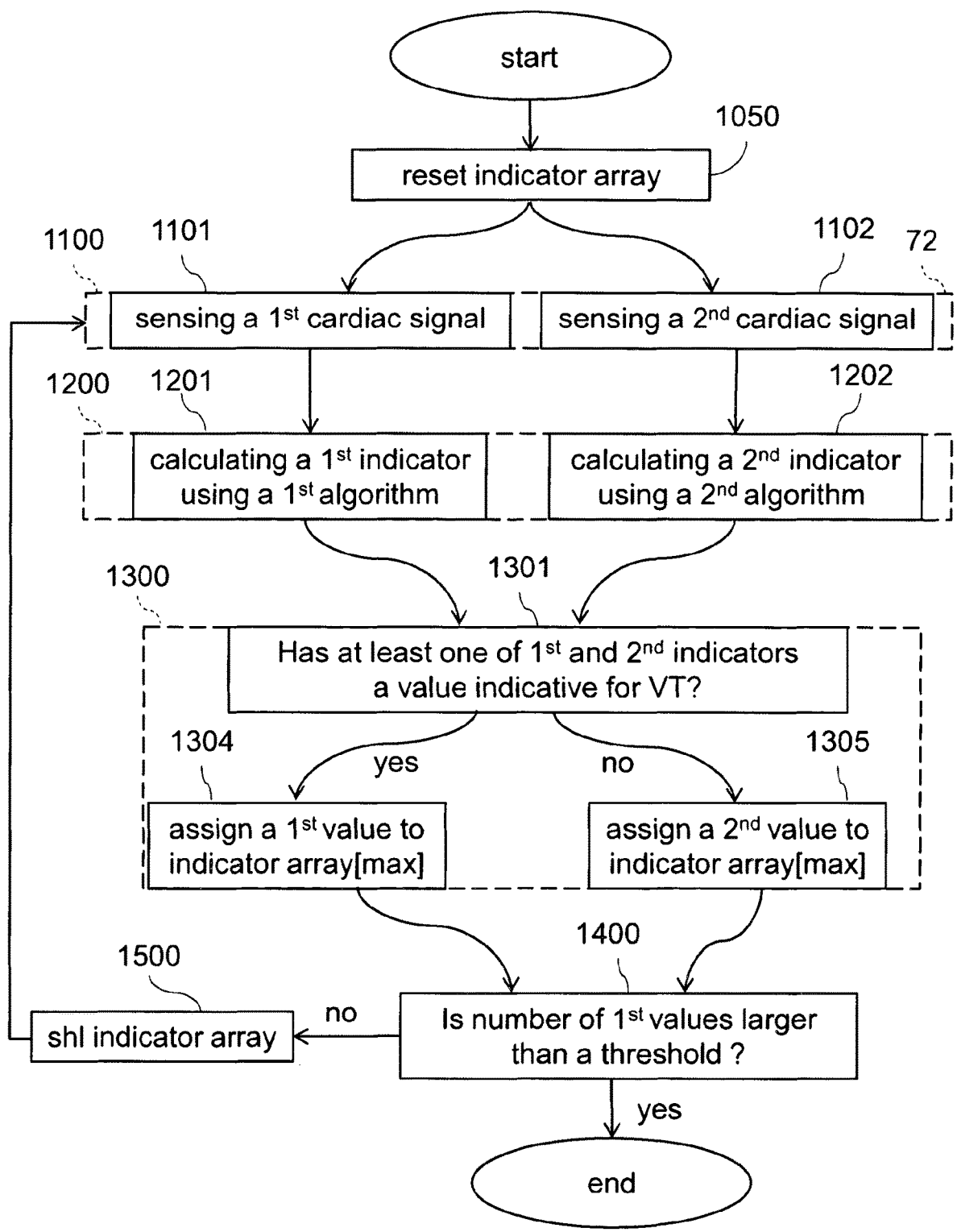
FIG. 5 is a flow chart of a method of automatically discriminating between an SVT-event and a VT-event according to an embodiment.

FIG. 5 is a flow chart of a method 1001 of automatically discriminating between SVT VT that may be executed by an IMD as explained above with regard to FIG. 1 to FIG. 3.

After detecting a tachycardia, e.g. by detecting a sudden increase in the heartrate, a sudden increase in the ventricular rate (RR-intervall), and/or an decrease in the variability of the ventricular rate, method 1001 may be started. For example, the ventricular rate may be monitored analyzing the near-field only on a beat-to-beat basis to detect a tachycardia. In one example, a tachycardia is detected when the ventricular rate is above a tachycardia threshold, which is typically in a range from about 160 bpm to about 180 bpm (beats per minute), after a sudden increase of e.g. at least 20 bpm. The tachycardia threshold for the ventricular rate or the heartrate may even be patient specific. Alternatively, an atrial rate may be monitored analyzing the far-field only on a beat-to-beat basis to detect the tachycardia.

In block 1050, an indicator array may be reset or initialized. In the exemplary embodiment, the indicator array is used for storing heartbeat-specific indicators, i.e. the indicator array is an array data structure of heartbeat-specific indicators. The heartbeat-specific indicators may be binary variables representing the tachycardia type of individual heartbeats detected within method 1001, in particular binary variables coding if an individual heartbeat is detected as being indicative for VT or SVT. In block 1050, the items (heartbeat-specific indicators) indicator array of may be initialized with a value representing SVT.

For example, a heartbeat-specific indicator value of zero may represent SVT and a heartbeat-specific indicator value of one may represent VT. Accordingly, the indicator array may be filled with zeros in block 1050. In an example, the indicator array is a bit array of suitable length, for example an integer number, such as an 8-bit integer for an indicator array with eight items.

In block 1100, a first cardiac signal is sensed using a first (cardiac) electrode pair (sub-block 1101) and a second cardiac signal is sensed using a second (cardiac) electrode pair (sub-block 1102). The first and second cardiac signals are cardiac signals relating to the same heartbeat. Thus, the first and second cardiac signals are typically sensed in parallel by a sensing module 72 as explained above with regard to FIG. 3.

In the exemplary embodiment, the first cardiac signal is more global than the second cardiac signal. Typically, the first cardiac signal is a relatively global EGM signal and the second cardiac signal is a relatively more local EGM signal. More typically, the first cardiac signal corresponds to a far-field cardiac signal (also referred to as FF-signal, in particular a far-field EGM signal) and the second cardiac signal corresponds to a near-field cardiac signal (also referred to as NF-signal, in particular a near-field EGM signal). It is however also possible that the first cardiac signal corresponds to a surface ECG (ElectroCardioGram) obtained with electrodes from the patient's surface or to an ECG obtained with housing electrodes of an IMD, and the second cardiac signal corresponds to an NF-signal.

In subsequent blocks 1201 and 1202, a first indicator and a second indicator may be determined (calculated) using a first comparison algorithm and a second comparison algorithm, respectively.

For sake of clarity, the method steps are in the following explained mainly with regard to FF-signals (far-field cardiac signals) and NF-signals (near-field cardiac signal) as first and second cardiac signals. Accordingly, determining the first indicator and the second indicator is in the following explained mainly with regard to a FF-indicator representing the first indicator and a NF-indicator representing the second indicator. However, this is to be understood as a non-limiting example.

The first comparison algorithm compares the FF-signal (first cardiac signal) with a first template corresponding to a typical normal far-field cardiac signal of the patient (far-field template, FF-template) to determine if the FF-signal is indicative for SVT or indicative for VT. Depending on the outcome, either a value representative for SVT (also referred to as svt-value or fourth value herein) or a value representative for VT (also referred to as vt-value or third value herein) may be assigned to the FF-indicator.

Likewise, the second comparison algorithm compares the NF-signal (second cardiac signal) with a second template corresponding to a typical normal near-field cardiac signal of the patient (near-field template, NF-template) to determine if the NF-signal is indicative for SVT or indicative for VT. Depending on the outcome, either the svt-value or the vt-value may be assigned to the NF-indicator.

The FF-indicator may be a (heartbeat-specific) QRS-indicator that is set in block 1201 according to detected deviations of QRS-morphology parameters. Accordingly, the first algorithm is typically configured to identify change(s) of Q-wave parameter(s), change(s) of R-wave parameter(s), and change(s) of S-wave parameter(s) in the FF-signal as compared to the FF-template. As such the first algorithm is typically set to analyze changes of heartbeat-specific morphology parameters referring to both negative waves, in particular Q-wave(s) and S-waves, and positive wave(s), in particular R-wave(s).

As explained above, reliability of discrimination between VT and SVT typically increases with the number of analyzed beat morphology parameter changes or deviations.

Therefore, the first comparison algorithm is typically set to determine (e.g. calculate) at least two heartbeat-specific morphology parameters, more typically at least four heartbeat-specific morphology parameters, and even more typically at least six heartbeat-specific morphology parameters in the FF-signal, and to compare these parameters with corresponding parameters of the FF-template.

To save computing time and reduce computing power, respectively, the morphology parameters of the FF-template are typically only calculated and stored in the device once, for example after recording a far-field signal of one or more normal heartbeats of the patient. The morphology parameters of the FF-template may also be determined at longer intervals to account for physiological changes of the patient's heart.

Typically, the third value is assigned to the heartbeat-specific QRS-indicator (thereby classifying the corresponding heartbeat as being indicative for VT) when at least one of the following far-field criteria for discriminating between VT and SVT is met:
  a) a number of Q-waves in the FF-signal differs from a number of Q-waves in the FF-template,
  b) a width of a Q-wave in the FF-signal is larger than a width of a Q-wave in the FF-template by at least about 30%,
  c) the width of the Q-wave in the FF-signal is smaller than the width of the Q-wave in the FF-template by at least about 20%,
  d) an amplitude of the Q-wave in the FF-signal is larger than an amplitude of the Q-wave in the FF-template by at least about 30% and a difference between an amplitude of an R-wave in the FF-signal differs from an amplitude of an R-wave in the FF-template by less than about 10%,
  e) the amplitude of the Q-wave in the FF-signal is smaller than the amplitude of the Q-wave in the FF-template by at least about 30%,
  f) a splitting of an R-wave in the FF-signal differs from a splitting of an R-wave in the first template,
  g) a notching of the R-wave in the FF-signal differs from a notching of the R-wave in the FF-signal template,
  h) a width of the R-wave in the FF-signal signal is larger than the width of the R-wave in the first template by at least about 20%,
  i) the width of the R-wave in the FF-signal is increased by at least about 12 ms compared to the width of the R-wave in the FF-signal or an averaged width of the R-wave during normal heartbeats, for example compared to the averaged width of eight R-waves during normal heartbeats in the FF-signal,
  j) the amplitude of the R-wave in the FF-signal is smaller than the amplitude of the R-wave in the FF-template by at least about 30%, and
  k) a number of S-waves in the FF-signal differs from a number of S-waves in the first template.

If none of the above far-field criteria a) to k) is met, the svt-value may be assigned to the heartbeat-specific QRS-indicator classifying the corresponding FF-signal of the heartbeat as being indicative for SVT.

The first comparison algorithm may however be set to use only a subset of the above described far-field criteria for determining the heartbeat-specific QRS-indicator. In these embodiments, the svt-value is assigned to the heartbeat-specific QRS-indicator when none of the far-field criteria of the sub-set is met.

The sub-set may be patient-specific. Accordingly, QRS-parameters that are of no or of very low relevance regarding discrimination of VT and SVT for a particular patient are not analyzed. This results in reducing average computational efforts and power consumption. Accordingly, recharging intervals may be prolonged.

However, the first comparison algorithm is typically set to use at least one far-field criterion referring to Q-wave(s), at least one far-field criterion referring to R-wave(s) and at least one far-field criterion referring to S-wave(s) to achieve high sensitivity and a high specificity of discriminating between VT and SVT.

In one embodiment, the first comparison algorithm is set to use a subset of the far-field criteria a) to f) and h) to k). This setting is found to result in high sensitivity and high specificity for almost all patients.

To reduce average computational efforts and power consumption, the order of analyzing the criteria regarding the QRS-morphology parameters may be set in accordance with computational effort and likelihood of occurrence. As it is found to be sufficient to classify a heartbeat as being indicative for VT when only one of the criteria is met, average computational efforts and power consumption is reduced when a criterion is analyzed first or as one of the firsts that may be calculated comparatively easy and/or is comparatively often met.

Typically, the first comparison algorithm is therefore set to identify change(s) of Q-wave parameter(s) first, followed by identifying change(s) of R-wave parameter(s), followed by identifying change(s) of S-wave parameter(s). However, the order may be patient-specific and/or may depend on implementation of numerical routines.

The NF-indicator may be a (heartbeat-specific) S-indicator that is set in block 1202 in accordance with deviation(s) of S-morphology parameter(s). Accordingly, the second algorithm is typically set to analyze only changes of heartbeat-specific morphology parameters referring to negative wave(s), in particular S-wave(s) in the NF-signal compared to the NF-template.

Typically, the vt-value is assigned to the heartbeat-specific S-indicator when at least one of the following near-field criteria for discriminating between VT and SVT is met:
  a) a number of S-waves in the NF-Signal differs from a number of S-waves in the NF-template,
  b) the NF-signal has compared to the NF-template an additional negative wave prior to an R-wave,
  c) the NF-signal has compared to the NF-template an additional negative wave after the R-wave,
  d) the NF-template has compared to the NF-signal an additional negative wave prior to the R-wave,
  e) the NF-template has compared to the NF-signal an additional negative wave after the R-wave,
  f) an amplitude of a negative wave in the NF-signal is larger than an amplitude of a negative wave in the NF-template by at least about 30%, and
  g) the amplitude of the negative wave in the NF-signal is smaller than the amplitude of the negative wave in the NF-template by at least about 30%.

If none of the near-field criteria a) to g) is met, the svt-value may be assigned to the heartbeat-specific S-indicator classifying the corresponding NF-signal of the heartbeat as being indicative for SVT.

The morphology parameters in the NF-template are typically only calculated once, and stored in the device once, for example after recording a near-field signal of one or more normal heartbeats of the patient. Accordingly, computing time and computing power may be reduced. The morphology parameters of the NF-template may also be determined at longer intervals to account for physiological changes of the patient's heart.

Similar as explained above for the first algorithm, the second comparison algorithm may be set to use a subset of the above described near-field criteria for determining the heartbeat-specific S-indicator (S-wave indicator). In these embodiments, the svt-value is assigned to the heartbeat-specific QRS-indicator when none of the near-field criteria of the sub-set is met.

However, the second comparison algorithm is typically set to use at least one near-field criterion referring to S-wave(s), more typically to use at least two near-field criteria referring to S-wave(s) in order to achieve high sensitivity and a high specificity of discriminating between VT and SVT.

In one embodiment, the second comparison algorithm is set to use a subset of the near-field criteria b) to g). This setting is found to result in high sensitivity and high specificity for almost all patients.

Further, the order of search for the near-field criteria regarding the S-morphology parameters may also be set in accordance with computational effort and likelihood of occurrence. This search order may also be set patient-specific.

Due to the higher information content in the far-field, the first comparison algorithm is typically set to determine more heartbeat-specific morphology parameters than the second comparison algorithm.

Accordingly, the second comparison algorithm is typically less complex than the first comparison algorithm.

Furthermore, the second comparison algorithm is typically qualitatively different from the first comparison algorithm (uses a different comparison or search strategy) at least as it typically addresses a different combination of beat-specific morphology parameters.

As indicated by the dashed block 1200, the first indicator and the second indicator may be calculated or determined in parallel in blocks 1201 and 1202.

According to an embodiment, block 1201 corresponds to comparing the FF-signal with the FF-template to determine if changes of a set of QRS-wave morphology parameters are indicative for SVT, and block 1201 corresponds to comparing the NF-signal with the NF-template to determine if changes of a set of S-wave morphology parameters are indicative for SVT.

In a subsequent block 1300, a further value indicative for VT (also referred to as first value herein), is assigned to the heartbeat-specific indicator stored in the highest position of the indicator array, e.g. lowest bit of an integer variable, when at least one of the FF-signal and the NF-signal has been determined to be indicative for VT in block 1200. In one embodiment, this is the case when at least one of the QRS-indicator (first indicator) and the S-indicator (second indicator) has the third value. For example, it is checked in block 1301 if the QRS-indicator (first indicator) and/or the S-indicator (second indicator) have the third value. If so, the first value is assigned to the heartbeat-specific indicator stored in the highest position of the indicator array in block 1304. Otherwise, a further value indicative for SVT (also referred to as second value herein) may be assigned to the heartbeat-specific indicator stored in the highest position of the indicator array in block 1305.

The first value and the third value may be identical. Further, the second value and the fourth value may be identical. It is, however, also possible to uses different values for classifying individual heartbeats as being indicative for VT (first value) and SVT (second value), respectively, and for classifying a FF-signal and a NF-signal of individual heartbeats as being indicative for VT (third value) and SVT (fourth value), respectively.

According to an embodiment, block 1200 corresponds to searching for at least one deviation of the near-field cardiac signal from a patient-specific near-field template with respect to S-waves that is indicative for VT, and to searching for at least one deviation of the far-field cardiac signal from a patient-specific far-field template at least with respect to R-waves (typically also with respect to Q-wave(s) and S-waves(s))) that is indicative for VT.

In this embodiment, block 1300 corresponds to classifying the heartbeat as being indicative for SVT when no deviation indicative for VT has been found during searching, and as being indicative for VT otherwise.

In a subsequent block 1400, it is checked if the number of first values in the indicator array is larger than a threshold of e.g. 5 for an indicator array of typical length eight. If so, method 1001 may classify the tachycardia episode as VT and be exited to initiate appropriate heart stimulation. Otherwise, the indicator array may be reordered in block 1500 so that a following heartbeat can be analyzed in a subsequent cycle beginning with block 1100.

Typically, a tachycardia episode is classified as being VT when at least M out of N heartbeats in a sequence of N consecutive heartbeats are determined to be indicative for VT. Typically, M is larger than half of N but smaller than N. For example, at least 6 out of 8 heartbeats have to be indicative for VT to classify the tachycardia episode as VT. In the following, N is also referred to as the first number and M is also referred to as the second number.

Typically, a fraction of heartbeats that has to be determined to be indicative for VT to justify classifying the tachycardia episode as VT is about ⅔, more typically about ¾ or even about ⅘.

In the exemplary embodiment, reordering of the indicator array is achieved by a shift-left operation (slip in block 1500. This is, however, only one example for efficiently realizing the process steps 1100 to 1500 in analysis module 600 of controller 500 explained above with regard to FIG. 3.

Figure 6:
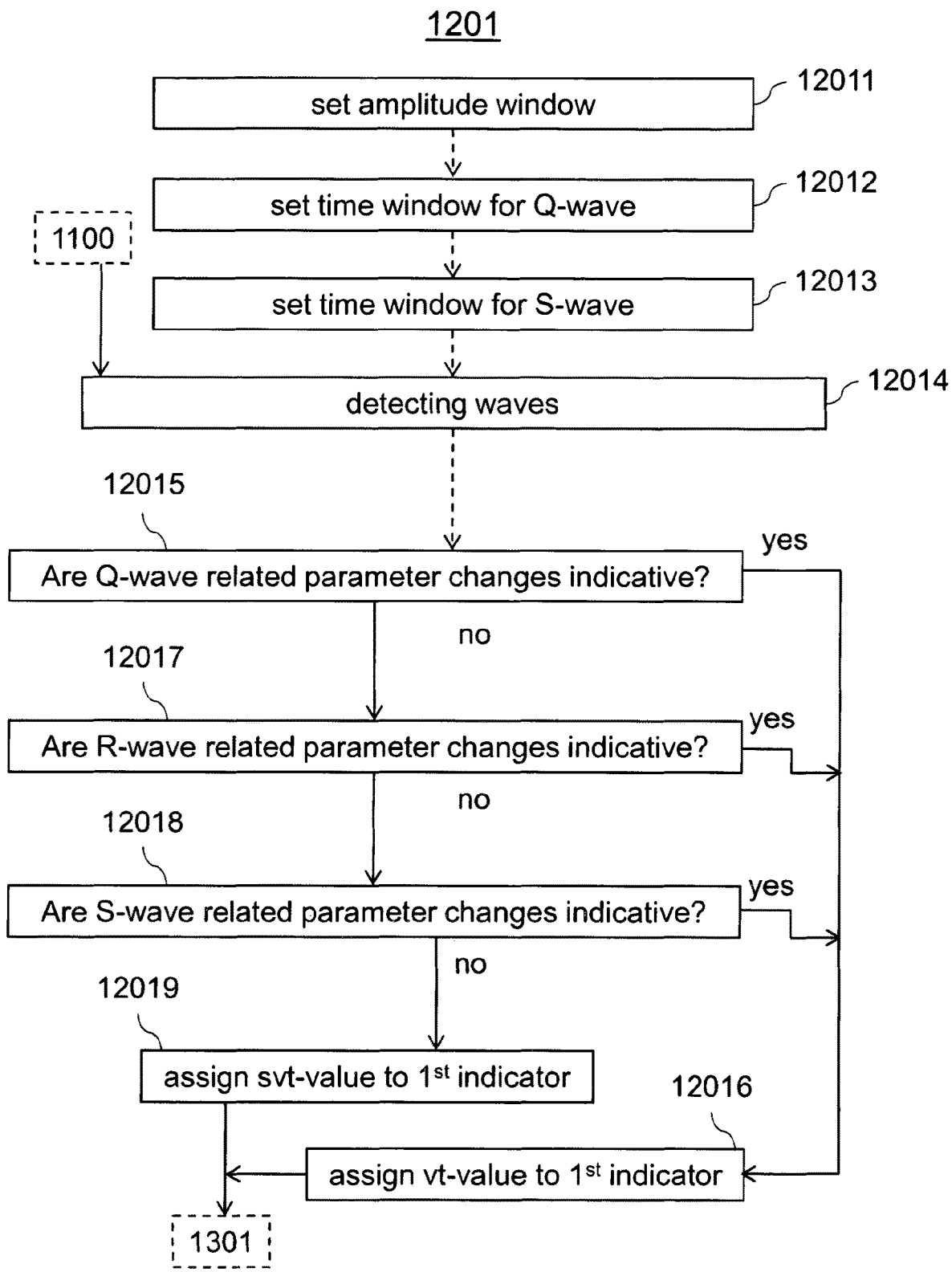
FIG. 6 is a flow chart of a method of automatically determining if a first cardiac signal is indicative for VT or SVT according to an embodiment.

FIG. 6 is a detailed flow chart of the method block (sub-routine) 1201 for determining if a FF-signal (first cardiac signal) corresponding to a heartbeat is indicative for VT or SVT and FIG. 5 is a detailed flow chart of the method block (sub-routine) 1202 for determining if a NF-signal (second cardiac signal) corresponding to the same heartbeat is indicative for VT or SVT as used by method 1001 explained above with regard to FIG. 5.

As explained above and illustrated in more detail in FIG. 6, for determining if the FF-signal is indicative for VT or SVT, it may first be checked if one or more Q-wave related morphology parameters are indicative for VT in block 12015. If so, the vt-value (third value) is assigned to the QRS-indicator (first indicator) in block 12016 and the sub-routine 1201 may be exited to return to block 1301 in FIG. 5. Otherwise, it is checked in block 12017 if one or more R-wave related morphology parameter are indicative for VT. If so, the vt-value is assigned to the QRS-indicator in block 12016. Otherwise, it is checked in block 12018 if one or more S-wave related morphology parameter are indicative for VT. If so, the vt-value is assigned to the QRS-indicator in block 12016. Otherwise, the svt-value may be assigned to the QRS-indicator in block 12019 and the sub-routine 1201 is exited to return to block 1301 in FIG. 5.

Prior to block 12015, the first comparison algorithm typically detects any Q-, R-, and S-waves in the FF-signal. In particular, the beginning of the waves may be detected.

Furthermore, an amplitude window (amplitude range at the base-line or iso-line of the NF-signal) to be ignored by the second comparison algorithm, a time window for detecting Q-waves and a time window for detecting S-waves and R-waves in the FF-signal (also referred to as common time window for detecting S-waves and R-waves in the FF-signal) may be set and/or adjusted in blocks 12011 to 12013. This may however only be done during initialization and is explained in more detail below with regard to FIG. 15 and following.

Figure 7:
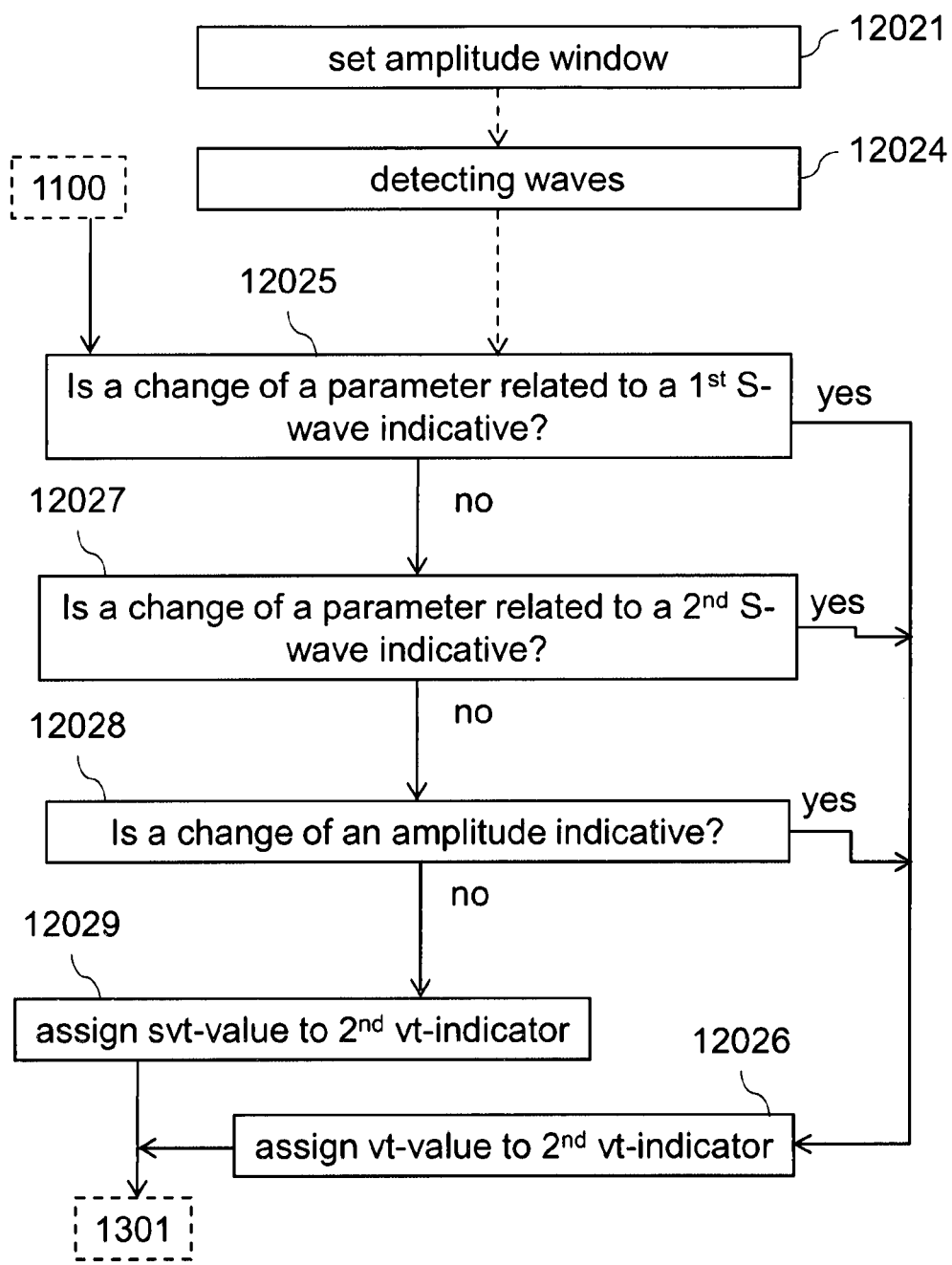
FIG. 7 is a flow chart of a method of automatically determining if a second cardiac signal is indicative for VT or SVT according to an embodiment.

As illustrated in FIG. 7, for determining if the NF-signal is indicative for VT or SVT, it may be first checked in block 12025 if a change of a morphology parameter related to a first S-wave is indicative for VT. If so, e.g. if a new S-wave in front of an R-wave is detected in the NF-signal compared to an NF-template or if a loss of an S-wave in front of the R-wave is detected in the NF-signal compared to the NF-template, the vt-value (third value) is assigned to the S-indicator (second indicator) in block 12026 and the sub-routine 1202 may be exited to return to block 1301 in FIG. 5. Otherwise, it may be checked in block 12027 if a change of a morphology parameter related to a second S-wave is indicative for VT. If so, e.g. if a new S-wave after the R-wave is detected in the NF-signal compared to the NF-template or if a loss of an S-wave after the R-wave is detected in the NF-signal compared to the NF-template, the vt-value is assigned to the S-indicator in block 12026. Otherwise, it may be checked in a block 12028 if a change of an amplitude is indicative for VT. If so, e.g. if the amplitude of at least one negative wave, in particular the amplitude of the largest S-wave in the NF-signal is detected to change by 30% or more compared the corresponding Q-wave or S-wave in the NF-template, the vt-value is assigned to the S-indicator in block 12026. Otherwise, the svt-value may be assigned to the S-indicator in block 12029 and the sub-routine 1202 is exited to return to block 1301 in FIG. 5.

Prior to block 12025, the second comparison algorithm typically detects any S-waves in the NF-signal. In particular, the beginning of the S-waves may be detected.

Furthermore, an amplitude window (amplitude range at the base-line or iso-line of the NF-signal) to be ignored by the second comparison algorithm, and an optional time window for detecting S-waves and R-waves in the NF-signal may be set and/or adjusted in blocks 12021 and 12022. This may however only be done during initializing. The time window for detecting S-waves and R-waves in the NF-signal is also referred to as common time window for detecting S-waves and R-waves in the NF-signal.

Figures 8A, 8B:
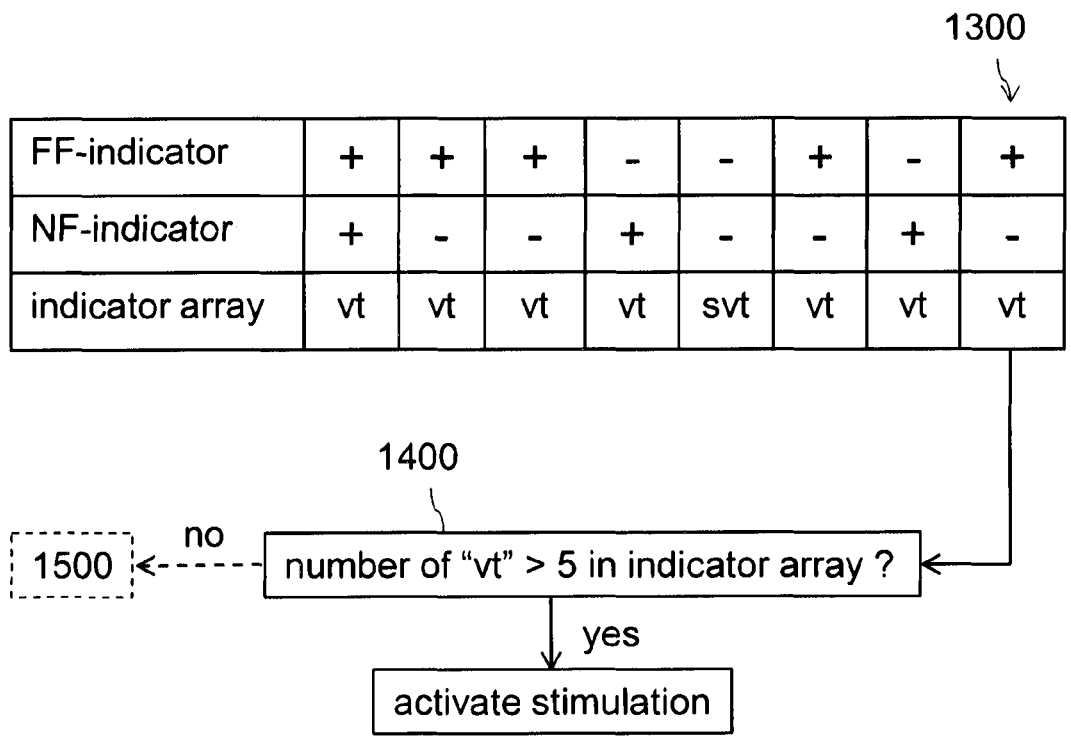
FIG. 8A is a logical table used in a method of automatically discriminating between an SVT-event and a VT-event according to an embodiment.
FIG. 8B illustrates the use of the logical table illustrated in FIG. 8A in a method of controlling stimulation energy in an IMD according to an embodiment.

FIG. 8A is a logical table 13011 used in block 1301 of the method for automatically discriminating between SVT and VT as illustrated in FIG. 5.

As can be seen, a heartbeat is identified as being indicative for VT ("vt" in the result row) if at least one of the FF-indicator and the NF indicator are identified as being indicative for VT ("+"). Only if both the FF-indicator and the NF-indicator are identified as being indicative for SVT ("−"), the heartbeat is identified as being indicative for SVT ("svt" in the result row). Accordingly, logical table 13011 represents an OR-logic.

Due to applying the OR-logic of logical table 13011 with "+" representing "true" and "−" representing "false" to the FF-indicator and the NF indicator determined as described with regard to FIG. 5 to FIG. 7, a sensitivity and specificity in discriminating between VT an SVT is achieved that is superior to other discrimination algorithms, in particular when the discrimination takes into account several heartbeats of a tachycardia episode.

FIG. 8B illustrates an example of use of the logical table illustrated in FIG. 8A, in which the evaluation of the indicator array in block 1400 of method 1001 results in classifying the tachycardia episode as VT although neither the eight FF-signals nor the eight corresponding NF-signals would be classified as VT when considered alone. This is because only three NF-indicators and only five FF-indicators have the third value "+" classifying the corresponding signal as being indicative for VT while the other have the svt-value "−" classifying the corresponding signal as being indicative for SVT.

In the exemplary embodiment, only half of the indicators have the third value "+". Still the algorithm correctly determines the tachycardia episode as VT. Accordingly, electric stimulation may be provided when needed.

A thorough (double-blind) test of the described method for automatically discriminating between VT and SVT with about 150 recorded tachycardia episodes revealed a sensitivity of about 99% and a specificity of about 90%. This is far superior compared to currently known wavelet based methods that reached at best a significantly lower sensitivity and a significantly lower specificity for the same tachycardia episodes. Therefore, the methods described herein detect more potentially life-threatening VTs correctly (increased sensitivity) and also misclassify less SVTs as VTs (increased specificity) than currently known automated methods. Accordingly, patients may be better protected against heart failure. Further, unnecessary delivery of stimulation to the ventricle(s) may be reduced. Given an incidence of SVTs of about 20% to 30% for tachycardia patients, unnecessary pain may be avoided and battery lifetime of IMDs may be increased to a significant extent.

In one embodiment, the first comparison algorithm is set to use a subset of the far-field criteria a) to f) and h) to k) and the second comparison algorithm is set a subset of the near-field criteria b) to g). In one non-limiting example, the first comparison algorithm applies far-field criteria a), b), c), d), and e), and the second comparison algorithm applies near-field criteria b), c), f), and g). The aforementioned settings are found to result in particularly high sensitivity and high specificity for almost all patients.

FIG. 9A illustrates the method steps 1050 to 1500 of method 1001 in better computer-suited or processor-suited implementation with zero as first value and as third value (vt-value), and one as second value and as fourth value (svt-value).

In block 1050, the indicator array is initialized with zeros. Assuming blocks 1201 and 1202 return ones for the first and second indicators (FF-indicator and NF-indicator) of the signals recorded in block 1100 (not shown in FIG. 9A), using the OR-operator in block 1300 results in storing a value of 1 in the last item of the indicator array. In block 1500, the items of the indicator array are shifted to the left.

FIG. 9B shows the situation illustrated in FIG. 9A after analyzing seven further heartbeats. FIG. 9B also corresponds to FIG. 8B. However, "+", "vt", "svt" are used as first value, third value, second value and fourth value, respectively, in FIG. 86. Different thereto, "1" is used as first value and third value, and "0" is used as second value and fourth value in FIG. 9B.

The embodiment illustrated in FIG. 9A and FIG. 9B is better suited for software implementation of method 1001. The shift-left operator of block 1500 is a fast and efficient bitwise operator. Further, checking if more than a predefined number of heartbeats is indicative for VT may be achieved by bitwise adding of items of the indicator array in block 1400.

Figure 10:
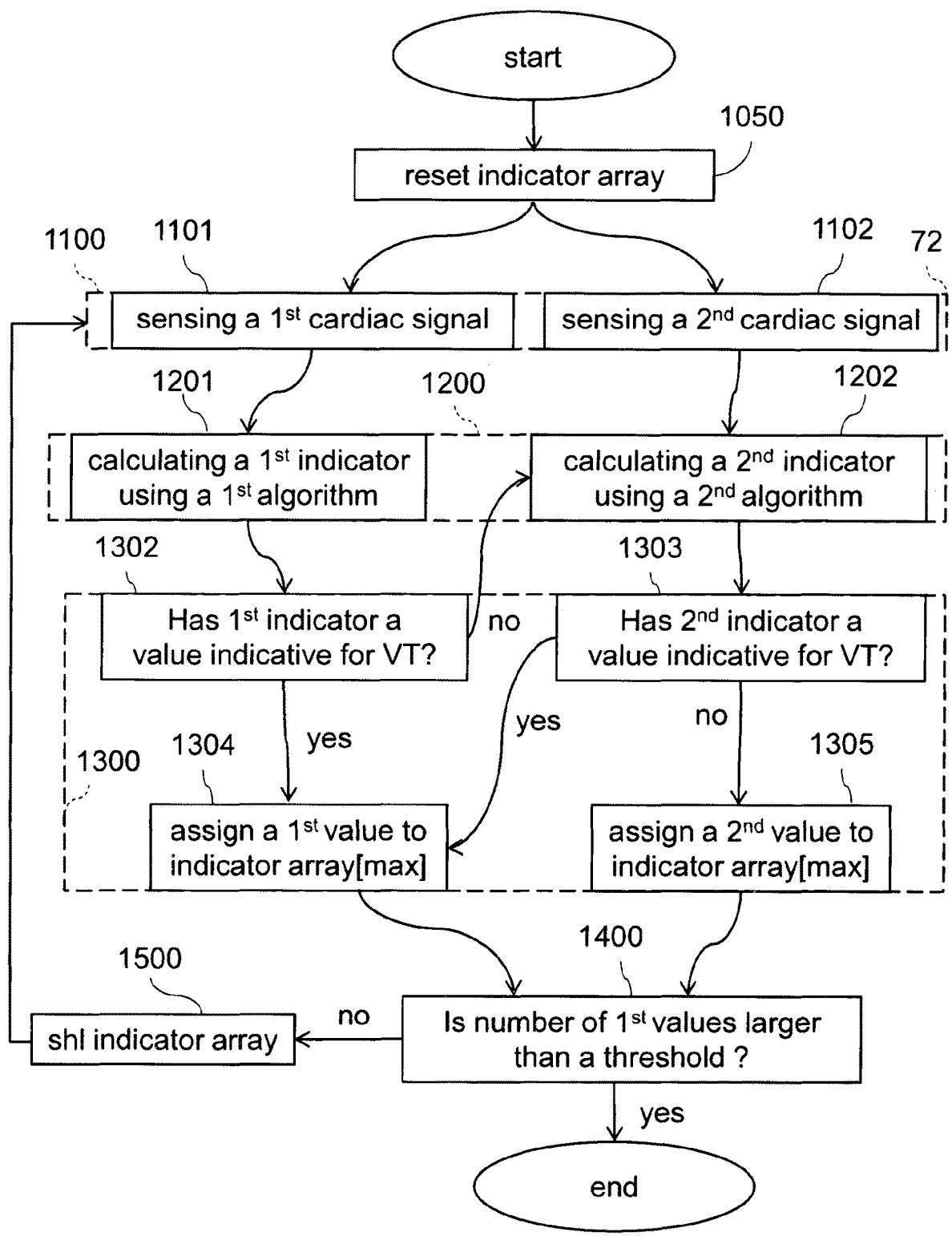
FIG. 10 is a flow chart of a method of automatically discriminating between an SVT-event and a VT-event according to an embodiment.

FIG. 10 is a flow chart of a method 1002 of automatically discriminating between SVT and VT-events. Method 1002 is similar to method 1001 explained above with regard to FIG. 5. However, the blocks 1201 and 1202 are not executed in parallel in FIG. 10.

In the exemplary embodiment illustrated in FIG. 10, block 1201 is executed after recording the cardiac signals in block 1100 to first determine if the FF-signal is indicative for VT (e.g. resulting in assigning the third value to the FF-indicator) or SVT (e.g. resulting in assigning the fourth value to the FF-indicator).

Thereafter, the first value is assigned to the last item of the indicator array in block 1304 when the FF-indicator (first indicator) has been set to the third value in block 1201. Otherwise, block 1302 is exited to block 1202 to determine if the NF-signal is indicative for VT (e.g. resulting in assigning the third value to the NF-indicator) or SVT (e.g. resulting in assigning the fourth value to the NF-indicator).

Thereafter, the first value is assigned to the last item of the indicator array in block 1304 when the NF-indicator (second indicator) has been set to the third value in block 1202. Otherwise, the first value is assigned to the last item of the indicator array in block 1304.

Compared to method 1001 explained above with regard to FIG. 5, method 1002 may be even more efficient as block 1202 may not be executed in each cycle. This may save battery lifetime.

In another embodiment, blocks 1202 and 1303 are executed prior to blocks 1201 and 1302.

Figure 11:
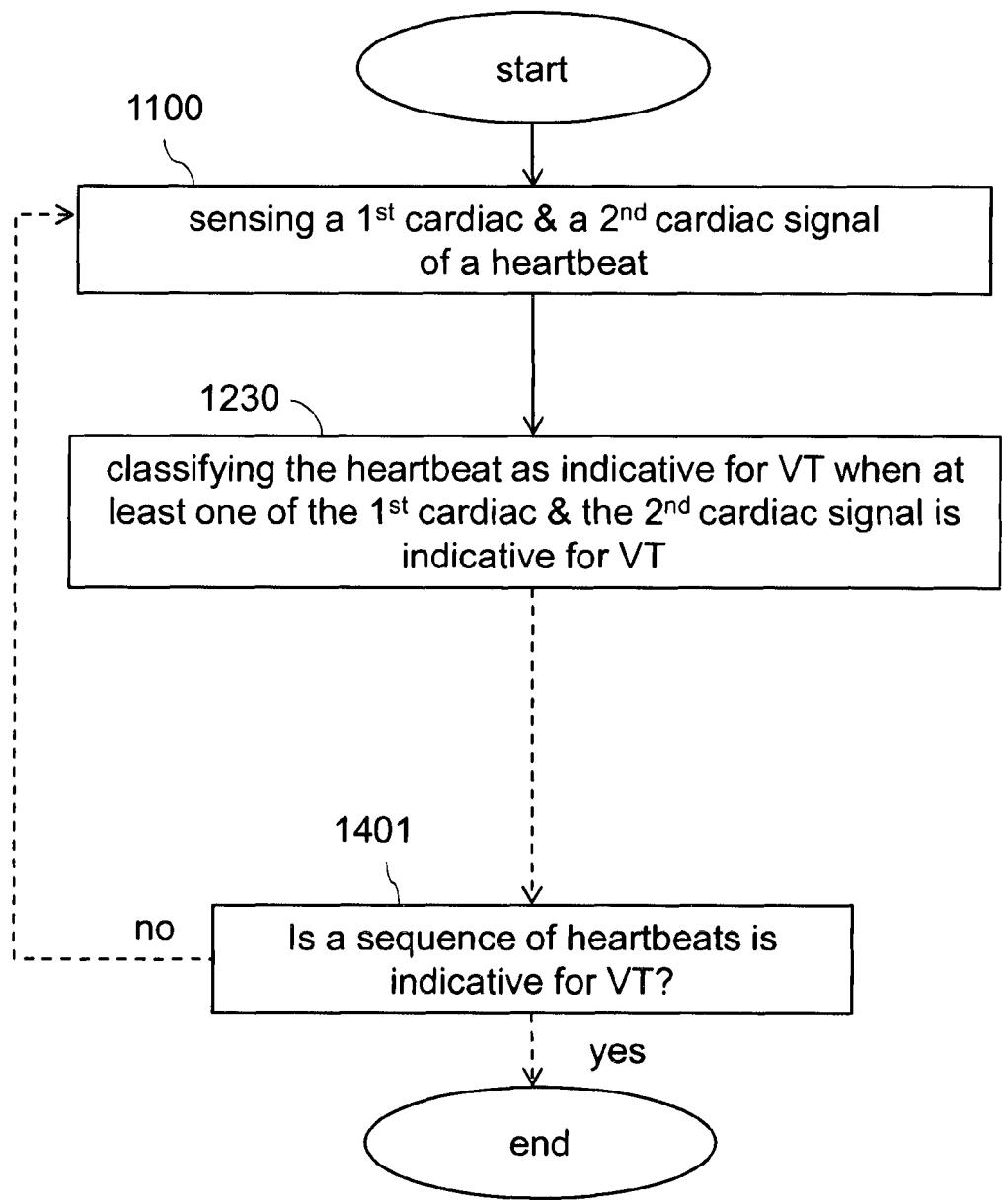
FIG. 11 is a flow chart of a method of automatically discriminating between an SVT-event and a VT-event according to an embodiment.

In an embodiment, methods 1001 and 1002 may be described as a method 1000 of sensing a first cardiac and a second cardiac signal in block 1100, and subsequently classifying the heartbeat as being indicative for VT when one of or both of the first cardiac and the second cardiac signal are classified as being indicative for VT in block 1230. Otherwise the heartbeat may be classified as being indicative for SVT. Method 1000 is illustrated in FIG. 11.

In an embodiment, block 1230 uses a detection algorithm to determine if two or more morphology parameters of waves in each of the two cardiac signals are indicative for VT. Thereafter, the heartbeat is classified as being indicative for VT if at least one of the morphology parameters is determined to be indicative for the ventricular tachycardia and as being indicative for SVT if none of the morphology parameters is determined to be indicative for the ventricular tachycardia.

The detection algorithm may use a first algorithm and a second algorithm as explained above. For example, block 1230 may include the blocks 1201 and 1202 as described above with regard to FIG. 5 and FIG. 10.

Instead of block 1230, method 1000 may have a block of classifying the heartbeat as being indicative for VT when none of the first cardiac and the second cardiac signal is indicative for SVT and as being indicative for SVT when the first cardiac and the second cardiac signal are both indicative for SVT, respectively.

Typically, method 1000 is exited for activating heart stimulation when a sequence of heartbeats is found to be indicative for VT in block 1401, more typically when at least a given number out of the predefined number of consecutive heartbeats, for example at least 6 out of 8 heartbeats are found to be indicative for VT.

Figure 12:
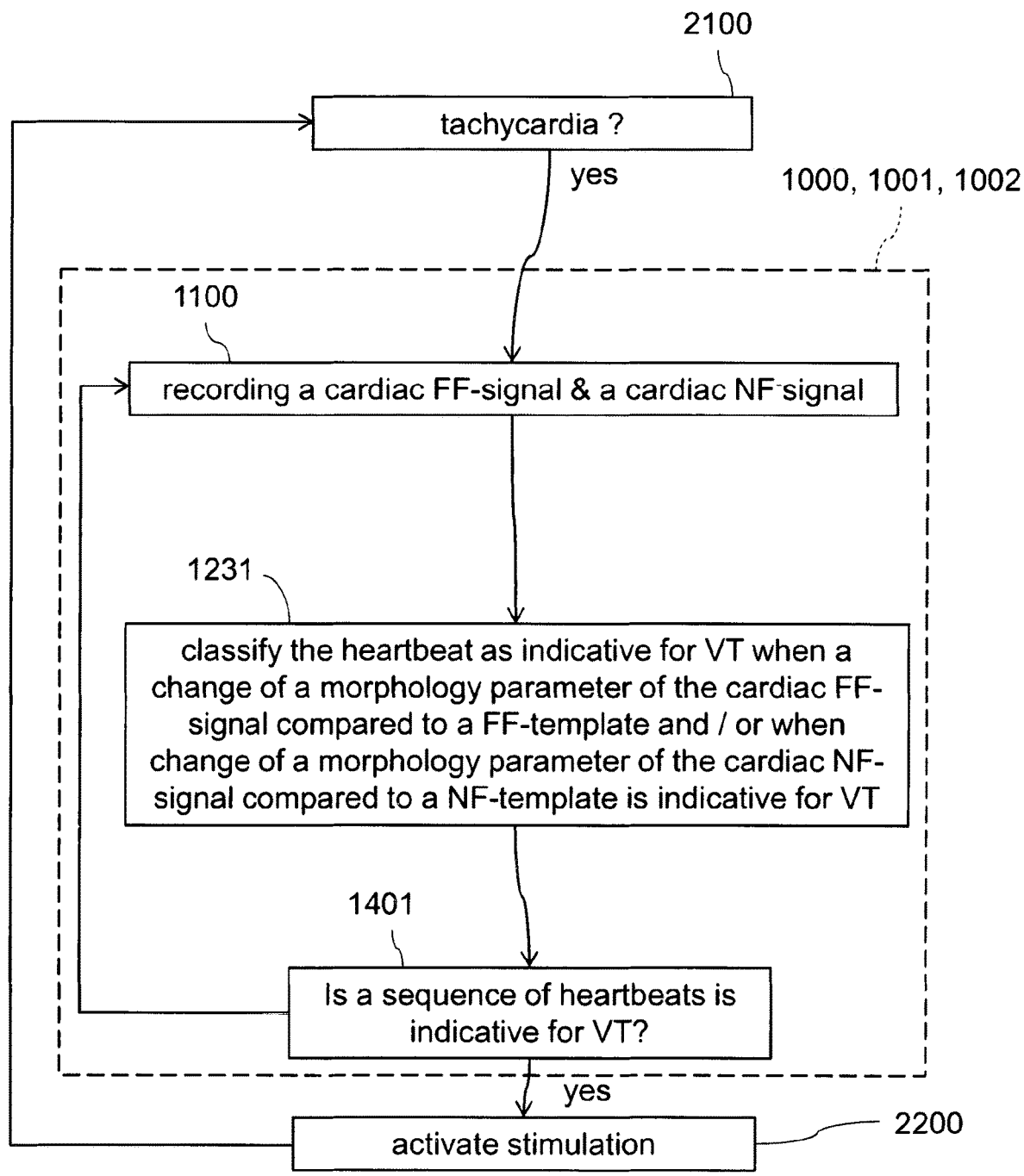
FIG. 12 is a flow chart of a method of treating tachycardia according to an embodiment.

FIG. 12 shows a flow chart of a method 2000 of treating tachycardia. After detecting a tachycardia in block 2100, any of the methods 1000, 1001 and 1002 for automatically discriminating between VT and SVT may be used to determine if a sequence of heartbeats is indicative for VT.

In the exemplary embodiment, illustrated in FIG. 12, in each cycle enclosed by the dashed rectangle, a cardiac FF-signal and a cardiac NF-signal of the same heartbeat are recorded in parallel in block 1100.

Thereafter, the heartbeat is in block 1231 classified as being indicative for VT when a change of a morphology parameter of the cardiac FF-signal compared to a FF-template is found to be indicative for VT using a first algorithm and/or when change of a morphology parameter of the NF-signal compared to a NF-template is found to be indicative for VT using a second algorithm different from the first algorithm.

For example, the first algorithm is set to search for morphology changes related to positive waves (in particular R-waves) and negative waves (in particular Q-waves and S-waves) and the second algorithm is set to search only for morphology changes negative waves (in particular S-waves).

In block 1401, the tachycardia is only identified as VT when a majority of heartbeats in a sequence is classified as being indicative for VT. If so, stimulation may be activated in block 2200.

After stimulation and a suitable delay time, method 2000 may return to block 2100.

Figure 13:
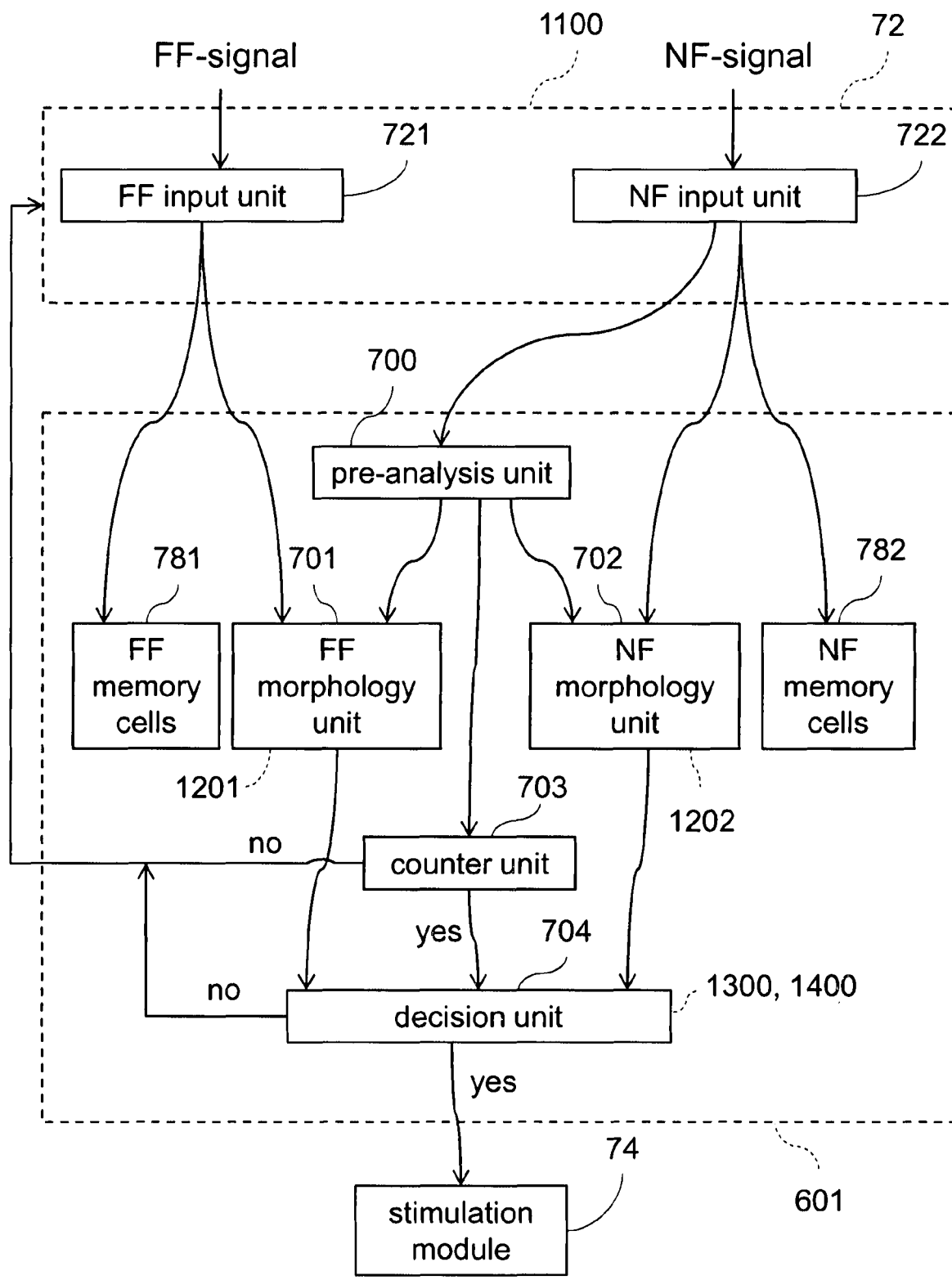
FIG. 13 illustrates a flow chart of an IMD control method and a functional block diagram of components of an IMD according to embodiments.

FIG. 13 illustrates a flow chart of a control method of an IMD as explained above with regard to FIG. 1 to FIG. 3 and a functional block diagram of components of a controller 501 of the IMD. Controller 501 is similar to controller 500 explained above with regard to FIG. 3 and has also a sensing module 72, a stimulation module 72 and an analysis module 601 with similar functionalities. However, analysis module 601 is shown in greater detail.

In order to sense in parallel an NF-signal and a FF-signal of a heartbeat, sensing module 72 of controller 501 has typically a corresponding far-field unit 721 and a corresponding near-field input unit 722. Each of the units 721, 722 may include an amplifier stage, a filter stage and a digitizer (AD-converter).

The digitized NF-signal and FF-signal may be stored in far-field and near-field memory cells 781, 782 of the memory of controller 501. The signals stored in memory cells 781, 782 may be retrieved via a telemetry module (not shown in FIG. 13) for external verification of the VT/SVT classifications made by controller 501.

After recording, the digitized NF-signal is typically pre-analyzed in a pre-analysis unit 700. Pre-analyzing typically includes identifying the beginning of the QRS-complex in the NF-signal. Pre-analysis unit 700 typically uses an amplitude window and a time window for detecting waves that may be patient-specific. As explained below with regard to FIG. 14A to FIG. 20C, using patient amplitude window and time windows increases performance of automatically discriminating VT and SVT.

The identified beginning of waves is used both in a far-field morphology unit 701 and a near-field morphology unit 702.

The far-field morphology unit 701 compares the FF-signal with a far-field template to analyze if changes of far-field morphology parameters are indicative for VT or SVT.

Likewise, the near-field morphology unit 702 compares the NF-signal with a near-field template to analyze if changes of near-field morphology parameters are indicative for VT or SVT.

In a decision unit 704 of controller 501 receiving the results of morphology units 701, 702, the heartbeat is marked as being indicative for VT if at least one of the near-field morphology parameters and the far-field morphology parameters is indicative for VT. Further, it is analyzed in decision unit 704 if a tachycardia episode is VT when a counter increased in each cycle in counter unit 703 is larger than a predefined number of e.g. eight or sixteen. If so, stimulation module may be activated. Otherwise, next heartbeat may be analyzed and classified.

Figure 14A:
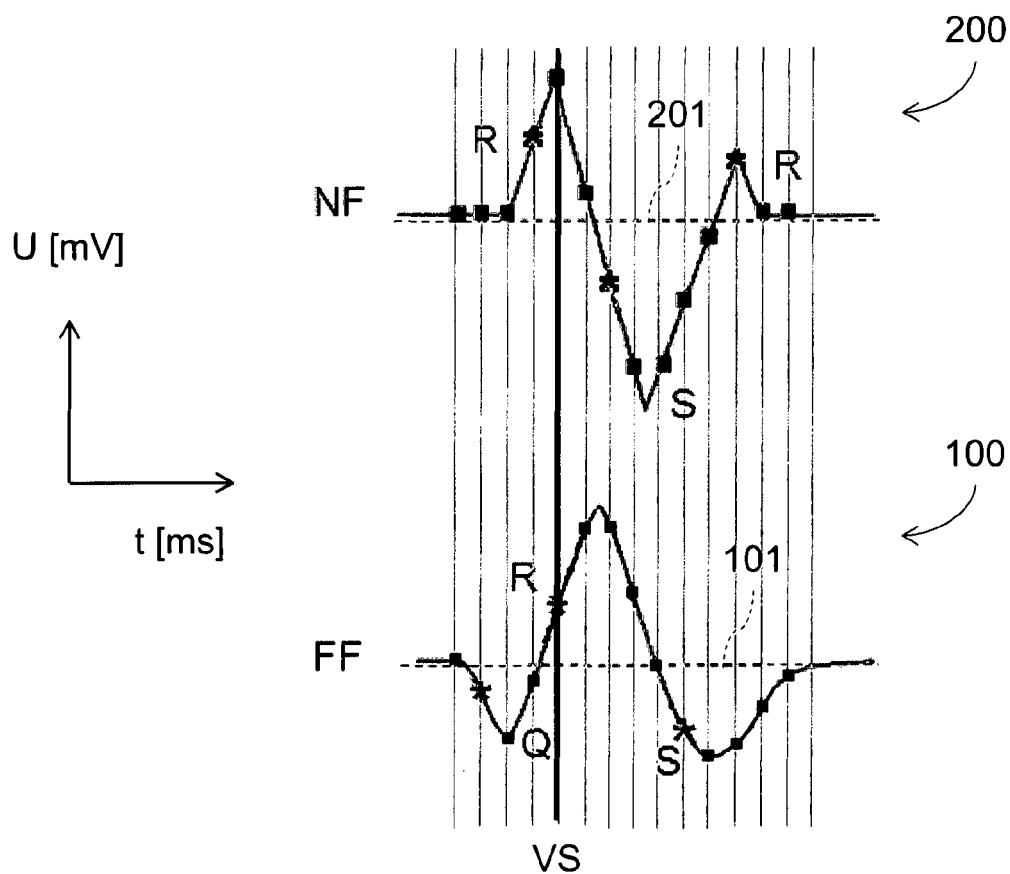
FIG. 14A and FIG. 14B illustrate cardiac signals during method steps of a method of automatically discriminating between an SVT-event and a VT-event according to an embodiment.

FIG. 14A shows a digitized FF-signal 100 and a digitized NF-signal 200 of heartbeat including information obtained by pre-analysis unit 700 as explained above with regard to FIG. 13. FF-signal 100 and NF-signal 200 were recorded simultaneously using a primary sampling rate which is higher than a secondary sampling rate of 4 ms corresponding to distance between vertical lines in FIG. 14A. The secondary sampling rate may also be smaller, e.g. 2 ms, or larger, e.g. 8 ms. Due to the secondary sampling, computational effort of subsequent routines may be reduced.

First, the QRS-complex may be detected in the recorded NF-signal 200. In particular, a time marker VS (ventricular sense) corresponding to a start time of the R-wave in the NF-signal 200 of the QRS-complex may be determined and used as for sampling the recorded FF-signal 100 and the recorded NF-signal 200 around the time VS with the secondary sampling rate. For sake of clarity, only a few of the digitized data points are represented as full squares in FIG. 14A. The dashed lines 101 and 201 correspond to isoelectric lines in the FF-signal 100 and NF-signal 200, respectively.

For secondary sampling, a QRS-time window of e.g. 96 ms around the time VS may be used. The QRS-time window of 96 ms may represent a Q-time window of e.g. 32 ms prior to the time VS and an RS-time window 104, 105 of e.g. 64 ms after to the time VS. The Q-time window and the RS-time window are in the following also referred to as Q-window and the RS-window, respectively. Typically, the length of the Q-window is about half the length of the RS-window 104, 105 in the FF-signal 100. However, the length of the Q-window, the length of the RS-window, and/or the length of the QRS-time window may be patient-specific. Typically, the length of the Q-window (reflecting an expected length of Q-wave(s)), and the length of the RS-window (reflecting an expected total length of R-wave(s) and S-wave(s) of QRS-complexes) are used as inputs for secondary digitizing.

The stars in the FF-signal 100 and the following drawings correspond to beginnings of the Q-wave, R-wave and S-wave determined by morphology unit 701 and 702 explained above with regard to FIG. 13.

Figure 14B:
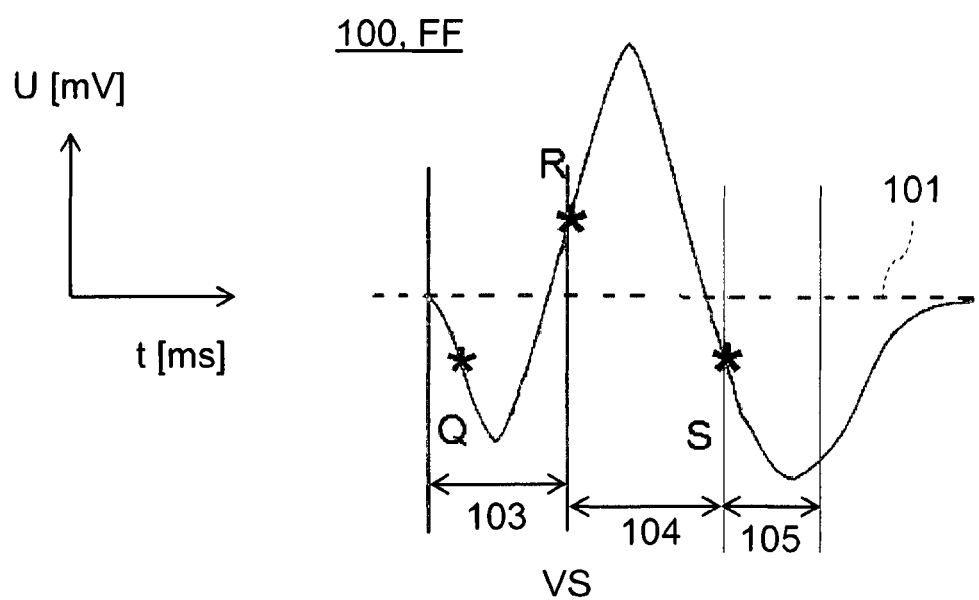

FIG. 14B shows an enlarged view of the FF-signal 100 including the Q-window 103, the RS-window 104, 105.

Figure 15:
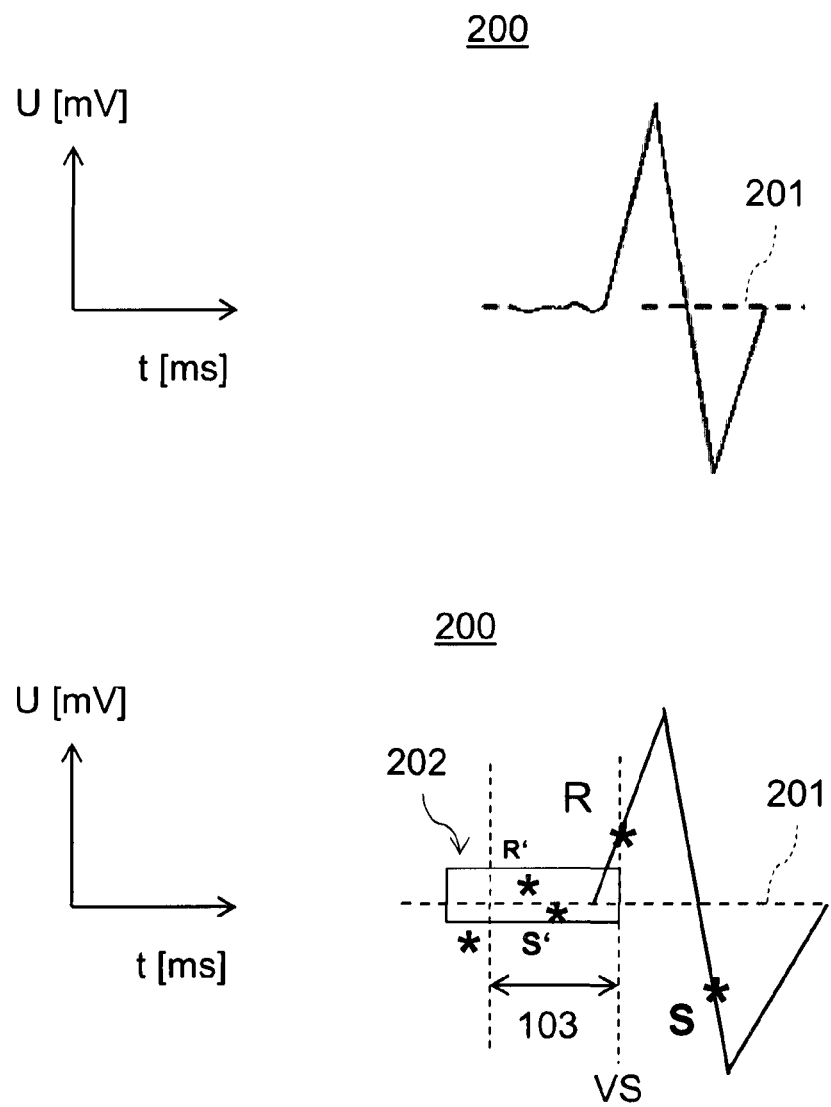
FIG. 15 illustrates a cardiac signal during a method steps of a method of automatically discriminating between an SVT-event and a VT-event according to an embodiment.

FIG. 15 shows an NF-signal 200 of another heartbeat after primary digitizing (upper figure) and secondary digitizing (lower figure). A cardiologist would recognize the primary digitized NF-signal 200 as an RS-configuration.

However, without setting an amplitude window 202 at the isoelectric line 201 in which data are to be ignored by the second algorithm, a further R-wave R' and a further S-wave S' would be erroneously detected.

To avoid misinterpreting noise as waves, an amplitude window 202 may be used. For the same reason, an amplitude window for data in the FF-signal to be ignored by the first comparison algorithm may also be set. This is explained below with regard to FIG. 16A to FIG. 16C.

A width of amplitude window 202 may be in a range from about 1% to about 20%, more typically in a range from about 5% to about 10% of an expected maximum amplitude of the R-wave(s), and/or S-wave(s), respectively.

Further, amplitude window 202 may be set asymmetrically with respect to the isoelectric line 201. Typically, amplitude window 202 is shifted to positive voltages. Accordingly, both weak negative waves, in particular low amplitude Q-waves may be safely detected and positive T-waves reliably masked.

Even further, amplitude window 202 is typically patient-specific to account for variability within patients. For example, amplitude window 202 may be set more asymmetrically with respect to isoelectric line 201 for patients with lower amplitude Q-waves compared to patients with higher amplitude Q-waves. For some patients with low amplitude Q-waves, amplitude window 202 may be shifted to about 25% towards positive voltages. For some patients with high amplitude Q-waves, amplitude window 202 may also be symmetric with respect to isoelectric line 201.

Figure 16A:
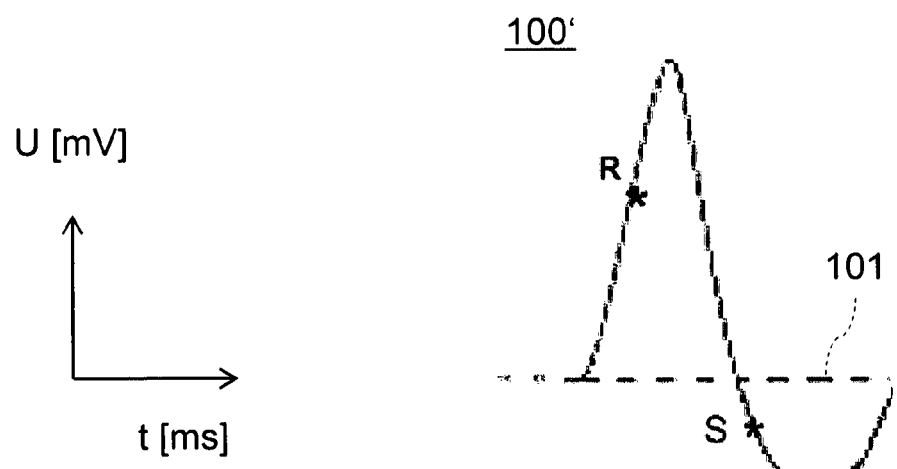
FIG. 16A illustrates a far-field cardiac signal of a patient's normal heartbeat.

FIG. 16A illustrates a FF-signal 100' of a patient's normal heartbeat. Far-field cardiac signal 100' and wave morphology parameters derived from FF-signal 100', respectively, may form the first template 100' used by the first comparison algorithm to determine if the first cardiac signal (100) is indicative for a supraventricular tachycardia or indicative for a ventricular tachycardia. A cardiologist will recognize the configuration of the QRS-complex shown in FIG. 16A as RS.

Figure 16B:
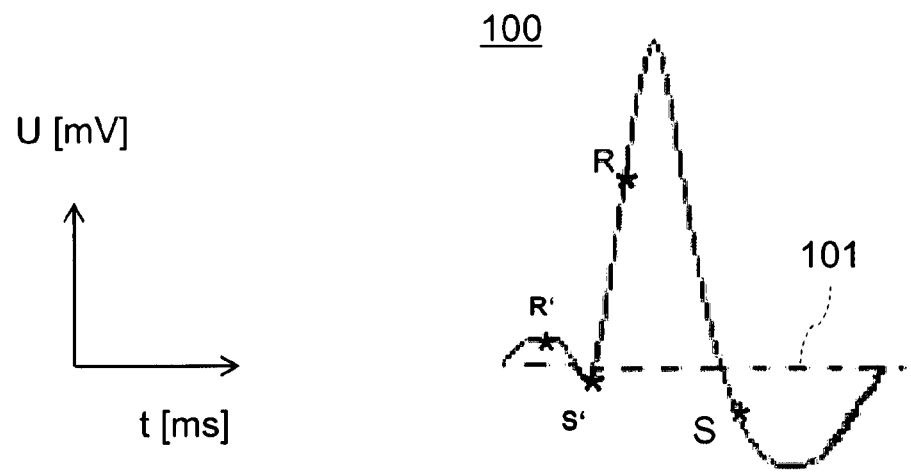
FIG. 16B and FIG. 16C illustrate far-field cardiac signals during method steps of a method of automatically discriminating between an SVT-event and a VT-event according to an embodiment.

FIG. 16B shows a FF-signal 100 of a further heartbeat of the same patient which was later recorded during a tachycardia by an implanted IMD. Taking into account all recorded data points, the algorithm would erroneously identify a further R-wave R' and a further S-wave S' compared to template 100'. Thus, the algorithm would erroneously classify the FF-signal 100 as a being indicative for VT.

However, the cardiologist will recognize the additional peaks R', S' in FF-signal 100 as being a tail of a T-wave. Accordingly, the cardiologist identifies the configuration of the QRS-complex (QRS-configuration) of FF-signal 100 also as being RS. Thus, the cardiologist classifies the FF-signal 100 as a being indicative for SVT.

Figure 16C:
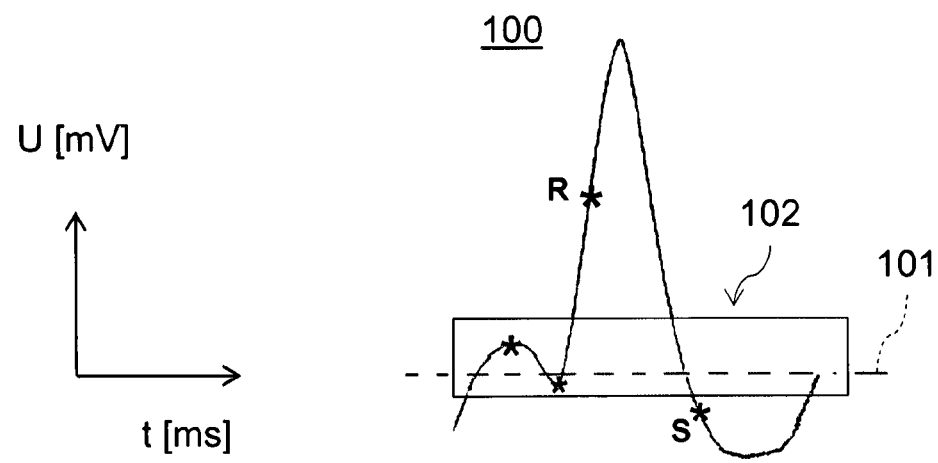

FIG. 16C illustrate the same FF-signals as in FIG. 16B, but with an additional amplitude window 102 at the isoelectric line 101 masking data points of low magnitude. Now, the automated algorithm identifies the ORS-configuration) of FF-signal 100 correctly as being RS. By comparing the QRS-configurations of FF-signal 100 and FF-signal 100', the algorithm classifies the FF-signal 100 as a being indicative for SVT.

A width of amplitude window 102 may be in range from about from 1% to 20%, more typically in a range from 5% to 10% of an expected maximum amplitude of the Q-wave(s), R-wave(s) and S-wave(s) and/or an expected QRS-amplitude, respectively.

Further, amplitude window 102 may be set asymmetric with respect to the isoelectric line 201. Typically, amplitude window 102 is shifted to positive voltages.

Even further, amplitude window 102 may patient-specific to account for variability within patients.

Figure 17A:
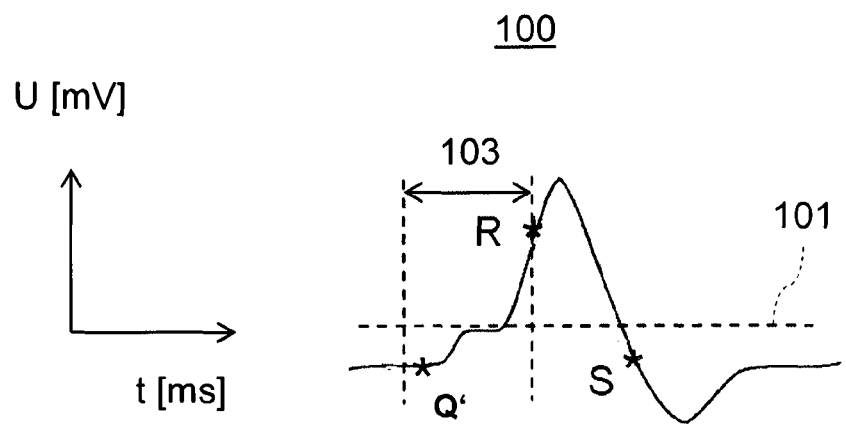
FIG. 17A and FIG. 17B illustrate cardiac signals during method steps of a method of automatically discriminating between an SVT-event and a VT-event according to an embodiment.
Figure 17B:
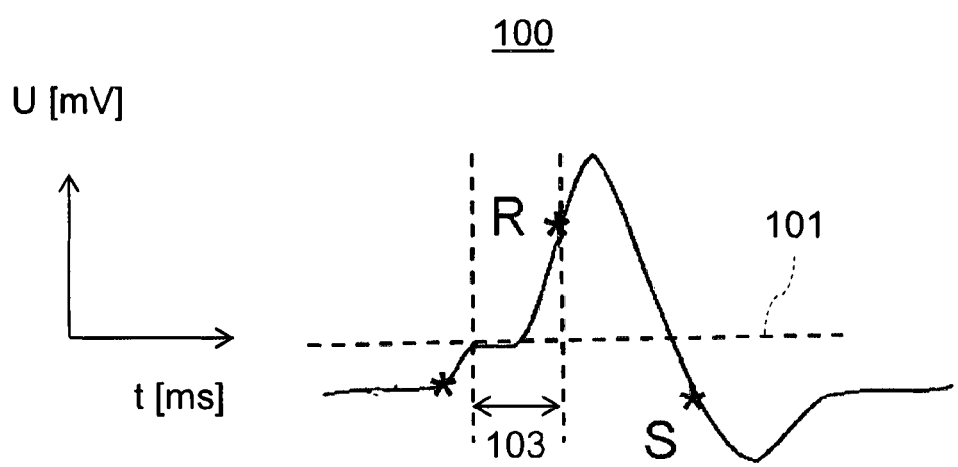

FIG. 17A and FIG. 17B show a FF-signal 100 of a heartbeat of a further patient after digitizing by an IMD as explained herein. Using the standard setting of a Q-window 103 of 32 ms length in FIG. 17A, the second algorithm may wrongly detect a Q-wave Q' instead of a tail of T-wave. As illustrated in FIG. 17B, this artefact may be avoided by reducing the length of the time window 103 for this patient. Accordingly, misclassifying FF-signal 100 as being indicative for VT may be avoided.

Depending on patient, Q-window 103 may have a width in a range from about 12 ms to about 64 ms, more typically in a range from about 16 ms to about 40 ms.

Figure 18A:
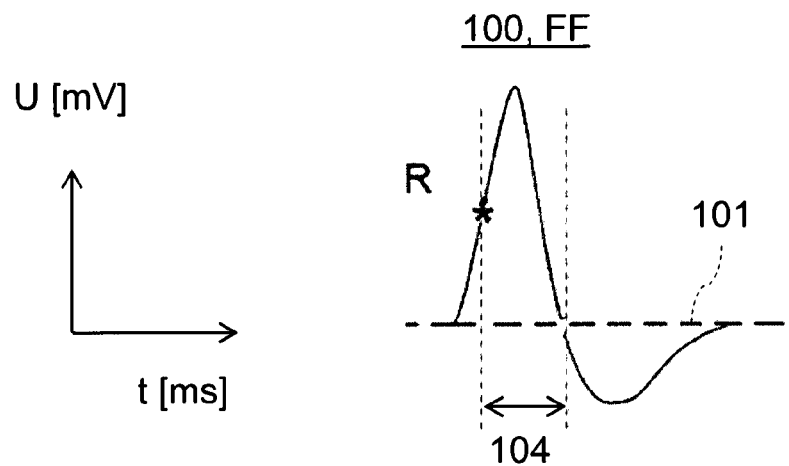
FIG. 18A and FIG. 18B illustrate cardiac signals during method steps of a method of automatically discriminating between an SVT-event and a VT-event according to an embodiment.
Figure 18B:
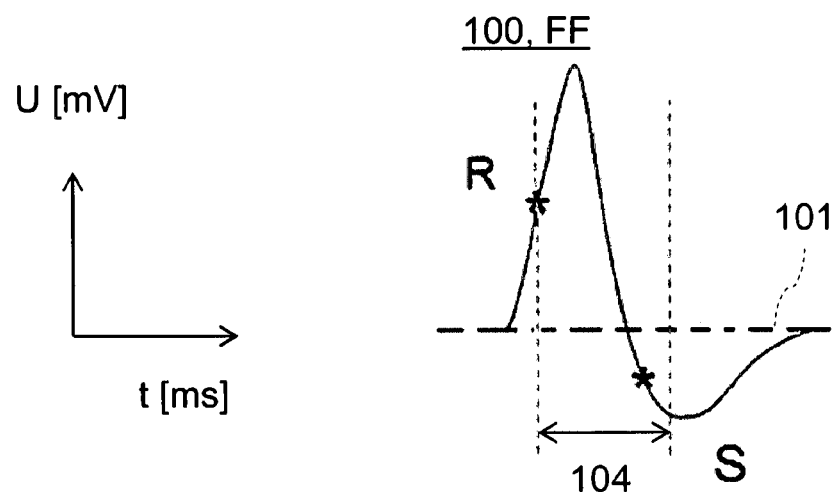

FIG. 18A and FIG. 18B show a FF-signal 100 of a heartbeat of a further patient after digitizing by an IMD as explained herein. A cardiologist will recognize the QRS-configuration as being RS. However, using the standard setting of the RS-window 104, 105 in FIG. 18A causes the algorithm to erroneously detect only an R-wave. As illustrated in FIG. 18B, this artefact may be avoided by increasing the length of the RS-window 104,105 for this patient.

Depending on the individual patient, RS-window 104, 105 may have a width in a range from about 12 ms to about 96 ms, more typically in a range from about 32 ms to about 72 ms.

Figure 19A:
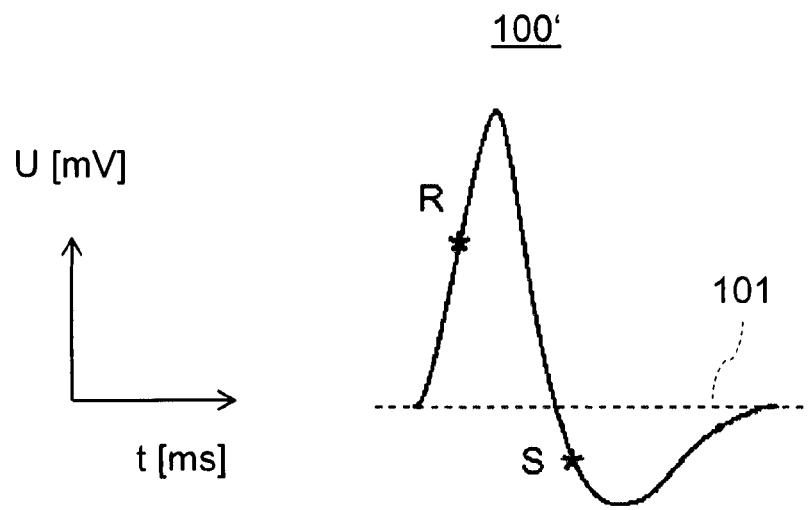
FIG. 19A and FIG. 19B illustrate cardiac signals during method steps of a method of automatically discriminating between an SVT-event and a VT-event according to an embodiment.

FIG. 19A illustrates a FF-signal 100' of a patient's normal heartbeat. FF-signal 100' or wave morphology parameters calculated from FF-signal 100' may form a FF-template.

Figure 19B:
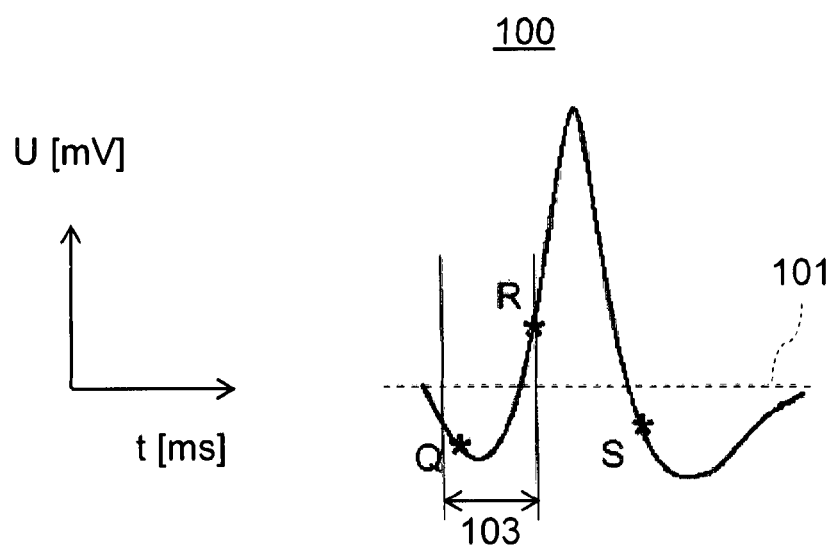

FIG. 19B illustrates a FF-signal 100 of a heartbeat during a tachycardia of the same patient. In this case, the algorithm correctly identifies an additional Q-wave in the FF-signal 100 and classifies this heartbeat correctly as being indicative for VT.

Detecting windows for the waves in the FF-signal(s) and the NF-signals (amplitude windows and time windows) as explained above are typically also used for analyzing normal heartbeats of a patient and calculating corresponding wave morphology parameters (templates).

Further, the physician or other user, in particular a cardiologist may adjust amplitude windows and/or time windows upon detecting a misclassification in the FF-signal(s) or the NF-signals(s) of normal heartbeats. Accordingly, misclassification of waves and wave-characteristics of signals representing normal heartbeats may be avoided and, thus, the reliability of discriminating VT and SVT increased.

Furthermore, the adjusted amplitude windows and time windows, respectively, may be used as patient-specific initial values for the corresponding parameters of the first algorithm and the second algorithm, respectively. The amplitude windows and time windows for the first algorithm and the second algorithm may later be adjusted by the physician or other user, in particular the cardiologist upon detecting a misclassification in the FF-signal(s) or the NF-signals(s) of heartbeat(s) during a tachycardia. Accordingly, the reliability of discriminating VT and SVT may be further increased.

Figure 20:
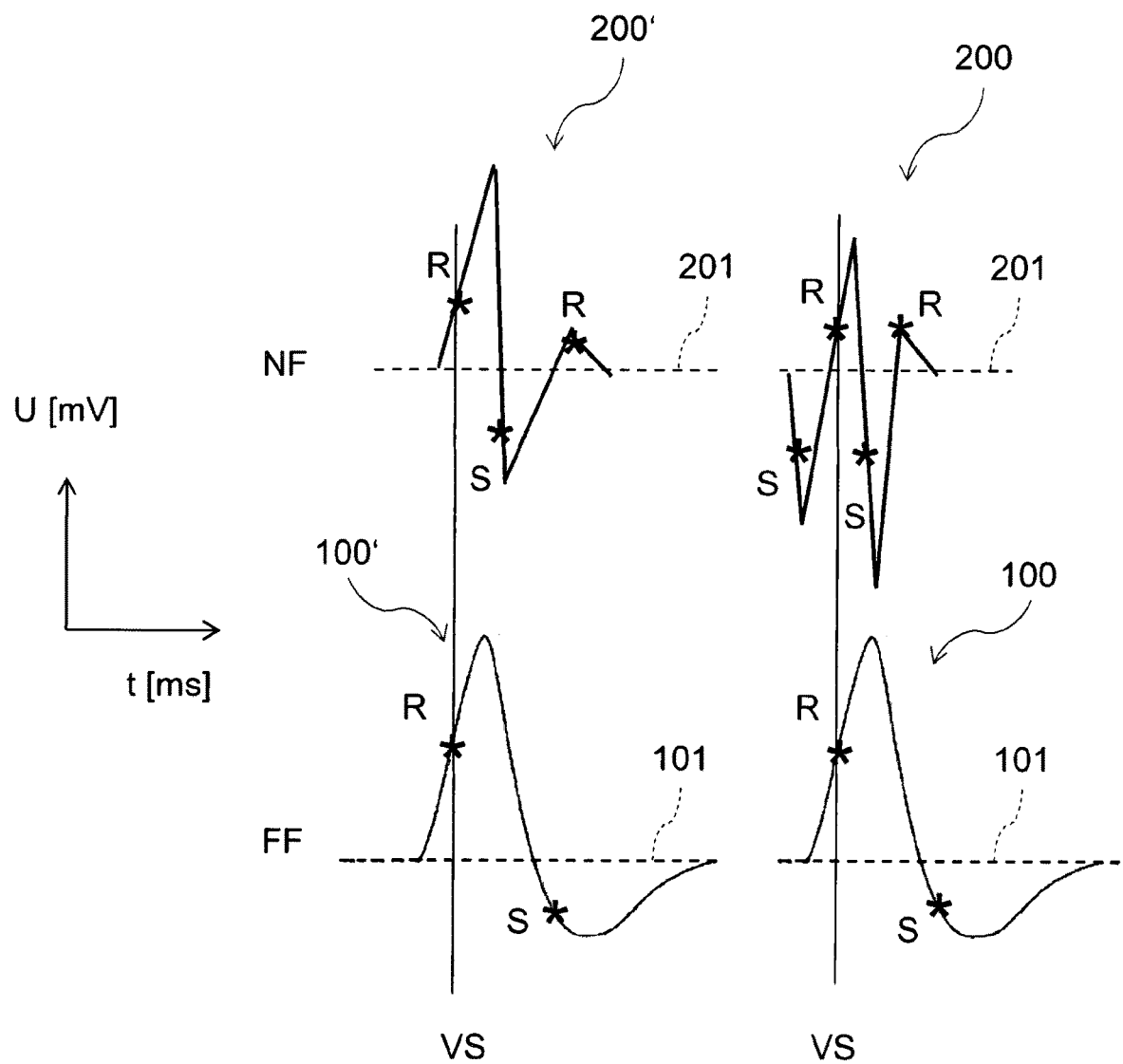
FIG. 20 illustrates cardiac signals during method steps of a method of automatically discriminating between an SVT-event and a VT-event according to an embodiment.

FIG. 20 illustrates a FF-signal 100' and an NF-signal 200' of a patient's normal heartbeat as well as a FF-signal 100 and an NF-signal 200 of a heartbeat during a tachycardia of the patient. FF-signal 100' or wave morphology parameters calculated from FF-signal 100' may form a FF-template used by the first comparison algorithm. NF-signal 200' or wave morphology parameters calculated from NF-signal 200' may form a NF-template used by the second comparison algorithm.

The first comparison algorithm analyzing FF-signal 100 does not find a morphology parameter change which is indicative for VT. However, the second comparison algorithm analyzing the NF-signal 200 detects a further S-wave in the NF-signal 200 compared to the NF-signal (NF-template) 200' and will, thus, correctly classify the heartbeat as being indicative for VT. This is one example illustrating that analyzing both the NF-signal 200 and the FF-signal 100 typically increases reliably of detecting VT.

Accordingly, automatically discriminating SVT and VT, typically includes recording two EGM-signals representing different spatial summation of action potential signals during a heartbeat, using an algorithm to determine if morphology parameters of waves in each of the two EGM-signals are indicative for a ventricular tachycardia, and classifying the heartbeat as being indicative for VT when at least one of the morphology parameters is determined to be indicative for VT and as being indicative for SVT when none of the morphology parameters is determined to be indicative for VT.

Although various exemplary embodiments of the invention have been disclosed, it will be apparent to those skilled in the art that various changes and modifications can be made which will achieve some of the advantages of the invention without departing from the spirit and scope of the invention. It will be obvious to those reasonably skilled in the art that other components performing the same functions may be suitably substituted. It should be mentioned that features explained with reference to a specific figure may be combined with features of other figures, even in those cases in which this has not explicitly been mentioned. Such modifications to the inventive concept are intended tote covered by the appended claims.

Spatially relative terms such as "under", "below", "lower", "over", "upper" and the like are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

What is claimed is:

1. A method for automatically discriminating between a supraventricular tachycardia and a ventricular tachycardia, the method comprising:

sensing a first cardiac signal using a first electrode pair during a heartbeat and sensing a second cardiac signal using a second electrode pair during the heartbeat, the second electrode pair having a different distance between its electrodes than the first electrode pair;

applying a first comparison algorithm to the first cardiac signal to determine whether the first cardiac signal is indicative for a supraventricular tachycardia or indicative for a ventricular tachycardia, wherein the first comparison algorithm uses a first template and is configured to compare the first cardiac signal to the first template to identify changes of first heartbeat-specific morphology parameters referring to negative waves and to positive waves;

applying a second comparison algorithm to the second cardiac signal to determine whether the second cardiac signal is indicative for the supraventricular tachycardia or indicative for the ventricular tachycardia, the second comparison algorithm being different from the first comparison algorithm, wherein the second comparison algorithm uses a second template different from the first template, and is configured to compare the second cardiac signal to the second template to identify changes of second heartbeat-specific morphology parameters referring to S-waves and/or Q-waves only; and classifying the heartbeat as being indicative for the ventricular tachycardia when at least one of the first cardiac signal and the second cardiac signal is determined to be indicative for the ventricular tachycardia.

2. The method of claim 1, wherein the first comparison algorithm is configured to determine more heartbeat-specific morphology parameters than the second comparison algorithm.

3. The method of claim 1, wherein each of the first comparison algorithm and the second comparison algorithm is configured to determine at least two heartbeat-specific morphology parameters.

4. The method of claim 1, comprising assigning to a heartbeat-specific indicator a first value indicative for the ventricular tachycardia when the heartbeat is classified as being indicative for the ventricular tachycardia.

5. The method of claim 4, wherein the first value is assigned to the heartbeat-specific indicator when at least one of the changes of the first heartbeat-specific morphology parameters and/or at least one of the changes of the second heartbeat-specific morphology parameters is indicative for the ventricular tachycardia, and/or wherein a second value indicative for a supraventricular tachycardia is assigned to the heartbeat-specific indicator when none of the changes of the first heartbeat-specific morphology parameters and none of the changes of the second heartbeat-specific morphology parameters is indicative for the ventricular tachycardia.

6. The method of claim 4, wherein the first comparison algorithm is configured to compare the first cardiac signal to a template to identify a change of a first Q-wave parameter, a change of a first R-wave parameter, and/or a change of a first S-wave parameter as respective first heartbeat-specific indicators.

7. The method of claim 6, wherein the first comparison algorithm is configured to identify the change of the first Q-wave parameter, the change of the first R-wave parameter, and the change of the first S-wave parameter in this order.

8. The method of claim 6, wherein the first comparison algorithm is configured to identify changes of several first Q-wave parameters, changes of several first R-wave parameters, and/or changes of the several S-wave parameters as respective first heartbeat-specific indicators.

9. The method of claim 4, wherein the heartbeat-specific indicator is determined for each of a first number of consecutive heartbeats, further comprising deciding that applying an electric stimulation signal to at least one of the first electrode pair and the second electrode pair is not required when the heartbeat-specific indicator of less than a second number of the consecutive heartbeats has the first value.

10. The method of claim 1, wherein the first cardiac signal corresponds to a far-field signal of the heartbeat, and/or wherein the first comparison algorithm is configured to assign to a heartbeat-specific QRS-indicator a third value indicative for the ventricular tachycardia when at least one of the first heartbeat-specific indicators is indicative for the ventricular tachycardia, and/or wherein the first comparison algorithm is configured to assign to the heartbeat-specific QRS-indicator a fourth value indicative for a supraventricular tachycardia when none of the first heartbeat-specific indicators is indicative for the ventricular tachycardia.

11. The method of the claim 10, wherein the third value is assigned to the heartbeat-specific QRS-indicator when a number of Q-waves in the first cardiac signal differs from a number of Q-waves in a template, when a width of a Q-wave in the first cardiac signal is larger than a width of a Q-wave in the template by at least about 30%, when the width of the Q-wave in the first cardiac signal is smaller than the width of the Q-wave in the template by at least about 20%, when an amplitude of the Q-wave in the first cardiac signal is larger than an amplitude of the Q-wave in the template by at least about 30% and when a difference between an amplitude of an R-wave in the first cardiac signal differs from an amplitude of an R-wave in the template by less than about 10%, and/or when the amplitude of the Q-wave in the first cardiac signal is smaller than the amplitude of the Q-wave in the template by at least about 30%.

12. The method of claim 10, wherein the third value is assigned to the heartbeat-specific QRS-indicator when a splitting of an R-wave in the first cardiac signal differs from a splitting of an R-wave in a template, when a notching of the R-wave in the first cardiac signal differs from a notching of the R-wave in the template, when a width of the R-wave in the first cardiac signal is larger than a width of the R-wave in the template by at least about 20%, when the width of the R-wave in the first cardiac signal is increased by at least about 12 milliseconds (ms) compared to the width of the R-wave in the cardiac template or an averaged width of R-waves during normal heartbeats, and/or when the amplitude of the R-wave in the first cardiac signal is smaller than the amplitude of the R-wave in the template by at least about 30%.

13. The method of claim 10, wherein the third value indicative for the ventricular tachycardia is assigned to the heartbeat-specific QRS-indicator when a number of S-waves in the first cardiac signal differs from a number of S-waves in a template.

14. The method of claim 1, wherein the second comparison algorithm is configured to compare the second cardiac signal to the second template to identify a change of an S-wave morphology parameter as a second heartbeat-specific indicator.

15. The method of claim 14, wherein the second comparison algorithm is configured to identify changes of several S-wave morphology parameters as second heartbeat-specific indicators.

16. The method of claim 1, wherein the second cardiac signal corresponds to a near-field signal of the heartbeat, and/or wherein the second comparison algorithm is configured to assign to a heartbeat-specific S-indicator a third value when at least one of the second heartbeat-specific morphology parameters is indicative for the ventricular tachycardia, and/or wherein the second comparison algorithm is configured to assign to the heartbeat-specific S-indicator a fourth value when none of the second heartbeat-specific morphology parameters is indicative for the ventricular tachycardia.

17. The method of claim 16, wherein the third value is assigned to the heartbeat-specific S-indicator when a number of S-waves in the second cardiac signal differs from a number of S-waves in a template, when the second cardiac signal has compared to the template an additional negative wave prior to an R-wave, when the second cardiac signal has compared to the template an additional negative wave after the R-wave, when the template has compared to the second cardiac signal an additional negative wave prior to the R-wave, when the template has compared to the second cardiac signal an additional negative wave after the R-wave, when an amplitude of a negative wave in the second cardiac signal is larger than an amplitude of a negative wave in the template by at least about 30%, and/or when the amplitude of the negative wave in the second cardiac signal is smaller than the amplitude of the negative wave in the template by at least about 30%.

18. The method of claim 16, wherein a first value is assigned to the heartbeat-specific indicator when the third value is assigned to at least one of the heartbeat-specific S-indicator and the heartbeat-specific QRS-indicator.

19. The method of claim 1, wherein none of the first comparison algorithm and the second comparison algorithm is based on a wave-let approach.

20. The method of claim 1, further comprising at least one of:
    setting an amplitude window for data in the first cardiac signal to be ignored by the first comparison algorithm;
    setting an amplitude window for data in the second cardiac signal to be ignored by the second comparison algorithm;
    setting a time window for detecting Q-waves; and
    setting a common time window for detecting S-waves and R-waves.

21. The method of claim 20, wherein at least one of the amplitude window, the time window for detecting Q-waves, and the common time window for detecting S-waves and R-waves is set patient-specific.

22. The method of claim 20, wherein a length of the common time window for detecting S-waves and R-waves is set to be about two times a length of the time window for detecting Q-waves.

23. The method of claim 20, wherein the amplitude window for the data in the first cardiac signal is set asymmetric with respect to an isoelectric line of the first signal.

24. The method of claim 1, wherein applying the first comparison algorithm comprises identifying waves in the first signal.

25. The method of claim 24, wherein applying the first comparison algorithm comprises determining properties of the identified waves in the first signal.

26. The method of claim 24, wherein applying the first comparison algorithm comprises comparing the identified waves in the first signal to waves in a template.

27. The method of claim 1, wherein applying the second comparison algorithm comprises identifying waves in the second signal.

28. The method of claim 27, wherein applying the second comparison algorithm comprises determining properties of identified negative waves in the second signal.

29. The method of claim 27, wherein applying the second comparison algorithm comprises comparing negative identified waves in the second signal to negative waves in a template.

30. The method of claim 1, further comprising at least one of determining the first template using the first electrode pair so that the first template is representative for a normal heartbeat of a patient, and determining the second template using the second electrode pair so that the second template is representative for the normal heartbeat.

31. The method of claim 1, prior to sensing the first cardiac signal further comprising at least one of detecting an increase in the heartrate, detecting an increase in the ventricular rate, and detecting a decrease in the variability of the ventricular rate.

32. A medical device, comprising:
    a first electrode pair;
    a second electrode pair having a different distance between its electrodes than the first electrode pair; and
    a controller connected with the first electrode pair and the second electrode pair and configured to:
        use the first electrode pair to determine a first cardiac signal of a heartbeat;
        use the second electrode pair to determine a second cardiac signal of the heartbeat;
        apply a first comparison algorithm to the first cardiac signal to determine whether the first cardiac signal is indicative for a supraventricular tachycardia or indicative for a ventricular tachycardia, wherein the first comparison algorithm uses a first template and is configured to compare the first cardiac signal to the first template to identify changes of first heartbeat-specific morphology parameters referring to negative waves and to positive waves;
        apply a second comparison algorithm to the second cardiac signal to determine whether the second cardiac signal is indicative for the supraventricular tachycardia or indicative for the ventricular tachycardia, the second comparison algorithm being different from the first comparison algorithm, wherein the second comparison algorithm uses a second template different from the first template, and is configured to compare the second cardiac signal to the second template to identify changes of second heartbeat-specific morphology parameters referring to S-waves and/or Q-waves only; and
        classify the heartbeat as being indicative for the ventricular tachycardia when at least one of the first cardiac signal and the second cardiac signal is determined to be indicative for the ventricular tachycardia.

33. The medical device of claim 32, wherein the medical device is an implantable pacemaker and/or an implantable cardioverter-defibrillator.

34. The medical device of claim 32, wherein the controller is configured to skip applying the second comparison algorithm to the second cardiac signal when the first cardiac signal has been determined to be indicative for the ventricular tachycardia, and/or to skip applying the first comparison algorithm to the first cardiac signal when the second cardiac signal has been determined to be indicative for the ventricular tachycardia.

35. The medical device of claim 32, wherein the first electrode pair and the second electrode pair share one common electrode.

36. The medical device of claim 32, wherein the analysis module is configured to classify the heartbeat as being indicative for the ventricular tachycardia and/or to assign a first value indicative for the ventricular tachycardia to a heartbeat-specific indicator when at least one of the changes of the first heartbeat-specific morphology parameters and/or at least one of the changes of the second heartbeat-specific morphology parameters is indicative for the ventricular tachycardia.

37. The medical device of claim 36, further comprising a stimulation module connected with the analysis module and configured to deliver stimulation energy to at least one of the second electrode pair and a further electrode pair connected to the stimulation module, wherein the analysis module is configured to control the stimulation module based on the heartbeat-specific indicators of a predefined number of consecutive heartbeats.

38. The medical device of claim 37, wherein the analysis module is configured to activate the stimulation module when the heartbeat-specific indicator of at least a given number out of the predefined number of consecutive heartbeats has the first value.

39. The medical device of any of the claim 32, further comprising a telemetry module connected with the analysis module to exchange data between the analysis module and a programming device, wherein at least one of the first comparison algorithm and the second comparison algorithm is adjustable by patient-specific parameters.

40. A computer readable storage medium comprising software code that, when executed by a processor of a medical device further comprising a first electrode pair and a second electrode pair having a different distance between its electrodes than the first electrode pair, causes the medical device to perform a method for automatically discriminating between a supraventricular tachycardia and a ventricular tachycardia, the method comprising:
sensing a first cardiac signal using the first electrode pair during a heartbeat and sensing a second cardiac signal using the second electrode pair during the heartbeat;
applying a first comparison algorithm to the first cardiac signal to determine whether the first cardiac signal is indicative for a supraventricular tachycardia or indicative for a ventricular tachycardia, wherein the first comparison algorithm uses a first template and is configured to compare the first cardiac signal to the first template to identify changes of first heartbeat-specific morphology parameters referring to negative waves and to positive waves;
applying a second comparison algorithm to the second cardiac signal to determine whether the second cardiac signal is indicative for the supraventricular tachycardia or indicative for the ventricular tachycardia, the second comparison algorithm being different from the first comparison algorithm, wherein the second comparison algorithm uses a second template different from the first template, and is configured to compare the second cardiac signal to the second template to identify changes of second heartbeat-specific morphology parameters referring to S-waves and/or Q-waves only; and
classifying the heartbeat as being indicative for the ventricular tachycardia when at least one of the first cardiac signal and the second cardiac signal is determined to be indicative for the ventricular tachycardia.

41. A method of treating tachycardia, the method comprising:
determining a far-field EGM signal relating to a heartbeat;
determining a near-field EGM signal relating to the same heartbeat;
comparing the far-field EGM signal with a far-field template EGM signal to determine first changes related to positive waves and negative waves;
comparing the near-field EGM signal with a near-field template EGM signal to determine second changes related to S-waves and/or Q-waves only;
assigning to a heartbeat-specific indicator a first value indicative for a ventricular tachycardia when at least one of the first changes and the second changes is indicative for the ventricular tachycardia; and
using the heartbeat-specific indicator to determine if an electric stimulation signal is to be delivered to at least two stimulation electrodes.

42. The method of claim 41, wherein the electric stimulation signal is delivered to at least two stimulation electrodes when the heartbeat-specific indicator of at least a second number of heartbeats in a sequence of a first number of heartbeats has the first value.

43. The method of claim 41, wherein the method is performed by an implantable medical device, wherein the implantable medical device comprises an implantable pacemaker and/or an implantable cardioverter-defibrillator.

44. The method of claim 41, wherein a second value indicative for a supraventricular tachycardia is assigned to the heartbeat-specific indicator when none of the first changes and the second changes is indicative for the ventricular tachycardia.

45. A method for automatically discriminating between a supraventricular tachycardia and a ventricular tachycardia, the method comprising:
recording two EGM-signals representing different spatial summation of action potential signals during a heartbeat;
using an algorithm to determine if morphology parameters of waves in each of the two EGM-signals are indicative for a ventricular tachycardia; and
classifying the heartbeat as being indicative for the ventricular tachycardia when at least one of the morphology parameters is determined to be indicative for the ventricular tachycardia and as being indicative for supraventricular tachycardia when none of the morphology parameters is determined to be indicative for the ventricular tachycardia,
wherein the morphology parameters in a first of the two EGM-signals refer to negative waves and positive waves, and the morphology parameters in a second of the two EGM-signals refer to S-waves and/or Q-waves only.

46. The method of claim 45, wherein the first of the two EGM-signals is a far-field EGM-signal of the heartbeat and the second of the two EGM-signals is a near-field EGM-signal, and wherein using the algorithm comprises comparing the morphology parameters of the waves in the far-field EGM-signal of the heartbeat with corresponding morphology parameters of waves in a far-field EGM-signal of a normal heartbeat and comparing the morphology parameters of the waves in the near-field EGM-signal of the heartbeat with corresponding morphology parameters of waves in a near-field EGM-template of the normal heartbeat.

* * * * *

UNITED STATES PATENT AND TRADEMARK OFFICE
CERTIFICATE OF CORRECTION

PATENT NO. : 11,229,396 B2
APPLICATION NO. : 15/567735
DATED : January 25, 2022
INVENTOR(S) : Ewald Himmrich It is certified that error appears in the above-identified patent and that said Letters Patent is hereby corrected as shown below:

In the Claims

On Column 35, Line 6 (Claim 39): Replace "device of any of the claim 32" with -- device of claim 32 --

Signed and Sealed this
Twenty-eighth Day of February, 2023

Katherine Kelly Vidal
*Director of the United States Patent and Trademark Office*